(12) United States Patent
Williams et al.

(10) Patent No.: US 11,317,945 B2
(45) Date of Patent: May 3, 2022

(54) TROCAR ASSEMBLIES FOR ADAPTER ASSEMBLIES FOR SURGICAL STAPLING INSTRUMENTS

(71) Applicant: Covidien LP, Mansfield, MA (US)

(72) Inventors: Justin Williams, Southbury, CT (US); Anthony Sgroi, Jr., Wallingford, CT (US); David Valentine, Jr., Hamden, CT (US); Jon Wink, Haddam, CT (US); Ramiro Cabrera, Cheshire, CT (US); Stephen Paul, East Hartford, CT (US)

(73) Assignee: Covidien LP, Mansfield, MA (US)

( * ) Notice: Subject to any disclaimer, the term of this patent is extended or adjusted under 35 U.S.C. 154(b) by 46 days.

(21) Appl. No.: 16/813,834

(22) Filed: Mar. 10, 2020

(65) Prior Publication Data

US 2020/0330127 A1    Oct. 22, 2020

Related U.S. Application Data

(60) Provisional application No. 62/834,490, filed on Apr. 16, 2019, provisional application No. 62/834,483, (Continued)

(51) Int. Cl.
*A61B 17/34* (2006.01)
*A61B 17/115* (2006.01)
*A61B 17/00* (2006.01)

(52) U.S. Cl.
CPC ....... *A61B 17/3468* (2013.01); *A61B 17/1155* (2013.01); *A61B 2017/00367* (2013.01);
(Continued)

(58) Field of Classification Search
CPC ............ A61B 17/1155; A61B 17/3468; A61B 2017/00367; A61B 2017/00473;
(Continued)

(56) References Cited

U.S. PATENT DOCUMENTS 3,193,165 A    7/1965  Akhalaya et al.
3,388,847 A    6/1968  Kasulin et al.
(Continued)

FOREIGN PATENT DOCUMENTS

CA         908529 A     8/1972
CA       2805365 A1     8/2013
(Continued)

OTHER PUBLICATIONS

European Search Report dated Sep. 8, 2020, corresponding to counterpart European Application No. 20169474.2; 8 pages.
(Continued)

*Primary Examiner* — Kathleen S Holwerda
*Assistant Examiner* — Brooke N Labranche
(74) *Attorney, Agent, or Firm* — Carter, DeLuca & Farrell LLP

(57) ABSTRACT

A trocar assembly for releasable engagement with an adapter assembly of a surgical stapling instrument includes a trocar mechanism that includes a trocar member that is at least one of rotatable or articulable relative to a housing of the trocar assembly.

20 Claims, 33 Drawing Sheets

Related U.S. Application Data filed on Apr. 16, 2019, provisional application No. 62/834,493, filed on Apr. 16, 2019, provisional application No. 62/834,486, filed on Apr. 16, 2019, provisional application No. 62/834,502, filed on Apr. 16, 2019.

(52) U.S. Cl.
CPC ............... *A61B 2017/00477* (2013.01); *A61B 2017/347* (2013.01)

(58) Field of Classification Search
CPC .... A61B 2017/00477; A61B 2017/347; A61B 2090/034
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |

(56) References Cited

U.S. PATENT DOCUMENTS

| | | |
|---|---|---|
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |

(56) References Cited

U.S. PATENT DOCUMENTS

| | | |
|---|---|---|
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |

(56) References Cited

U.S. PATENT DOCUMENTS

| | | |
|---|---|---|
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0224345 A1 | 8/2017 | Cabrera et al. |
| 2017/0281185 A1* | 10/2017 | Miller .................. A61B 17/115 |
| 2017/0340351 A1 | 11/2017 | Sgroi, Jr. |
| 2018/0042606 A1 | 2/2018 | Williams et al. |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 0634144 A1 | 1/1995 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3560438 A1 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2017172926 A1 | 10/2017 |

OTHER PUBLICATIONS

European Search Report dated Jul. 31, 2020, issued in EP Appln. No. 20169394, 8 pages.

European Search Report dated Aug. 20, 2020, issued in EP Appln. No. 20169397, 8 pages.

\* cited by examiner

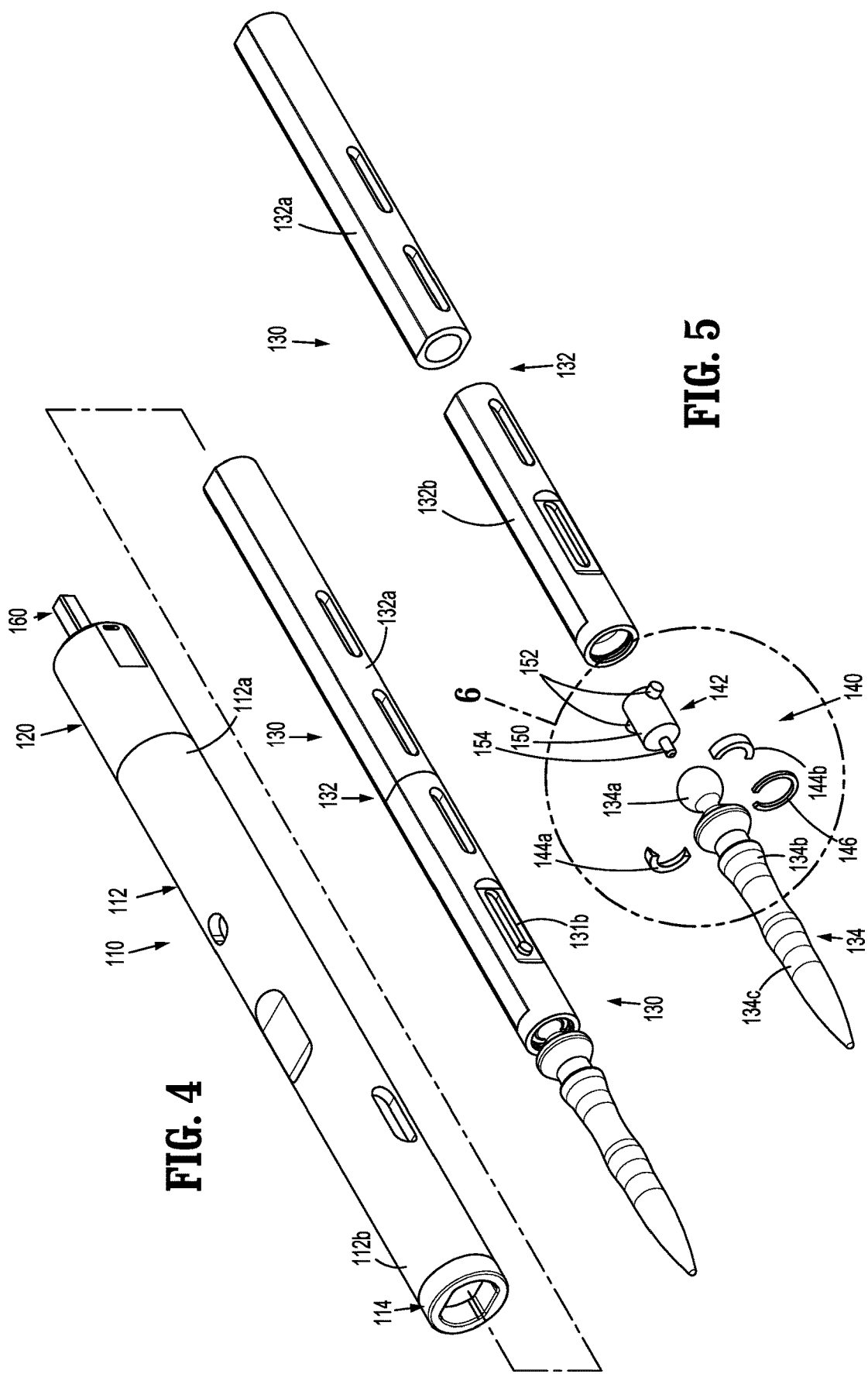

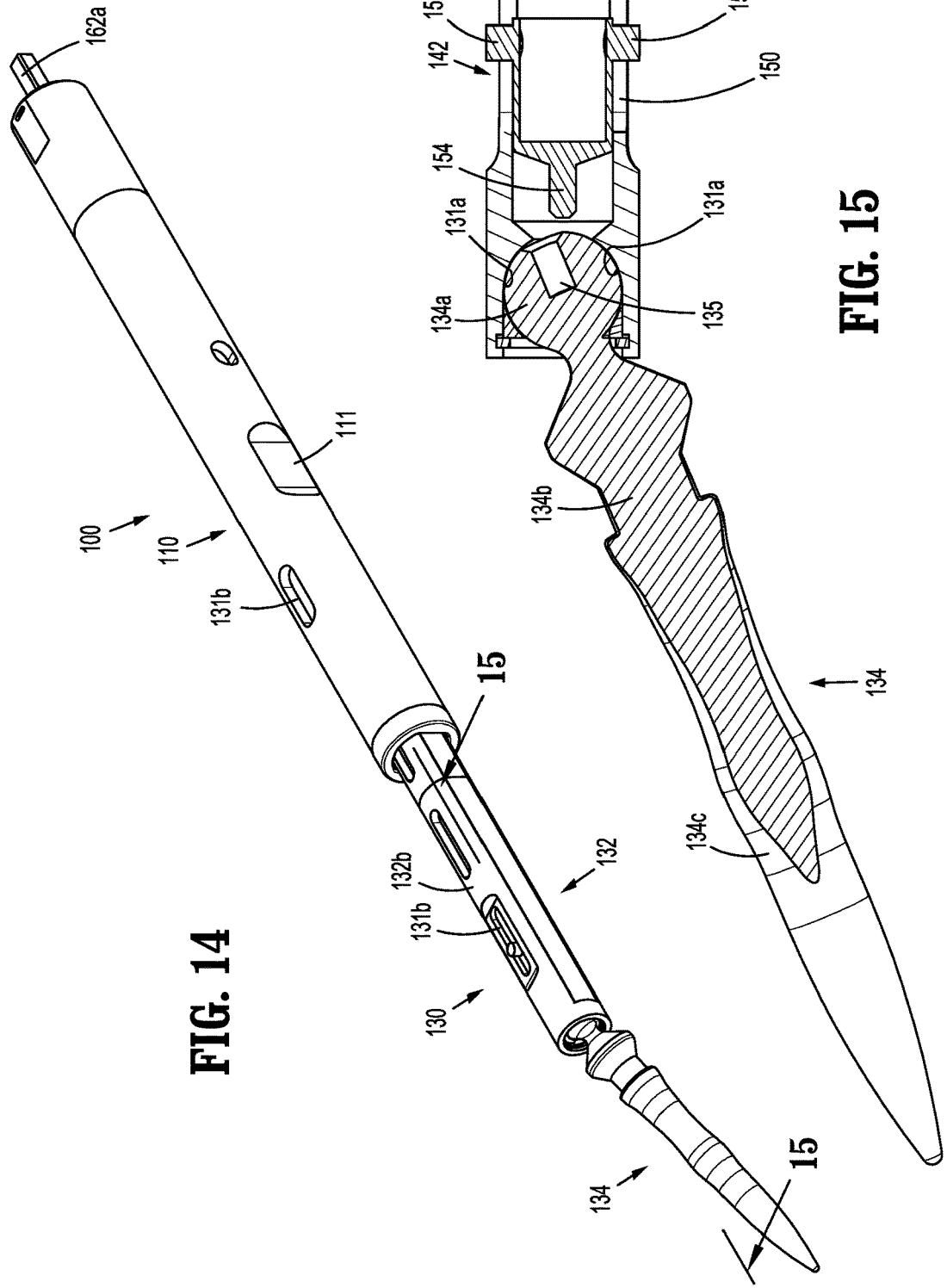

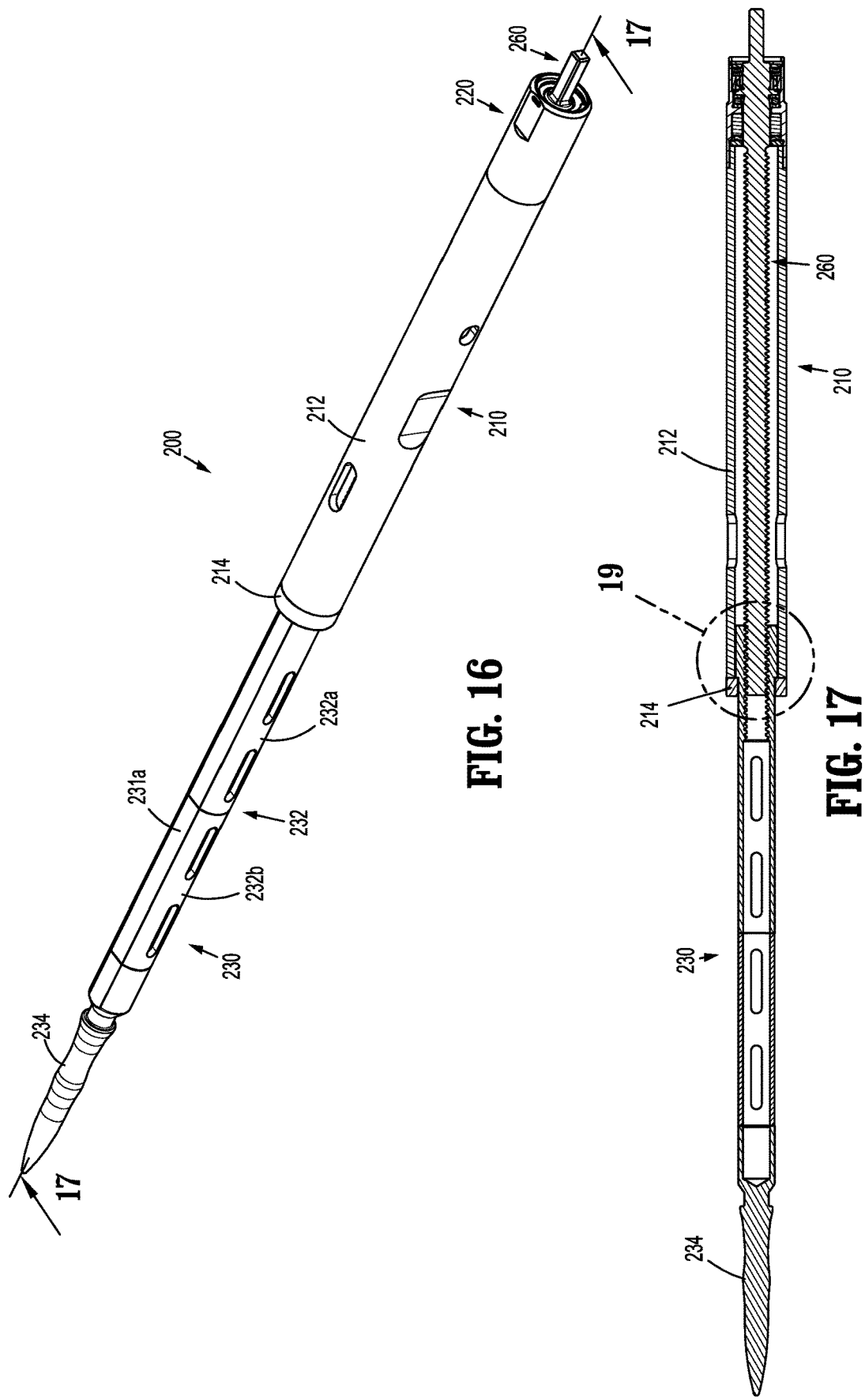

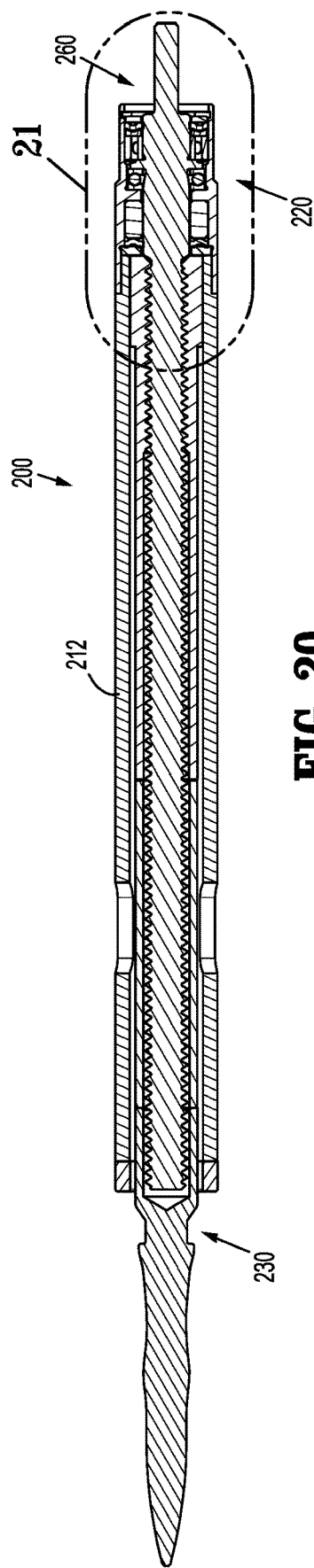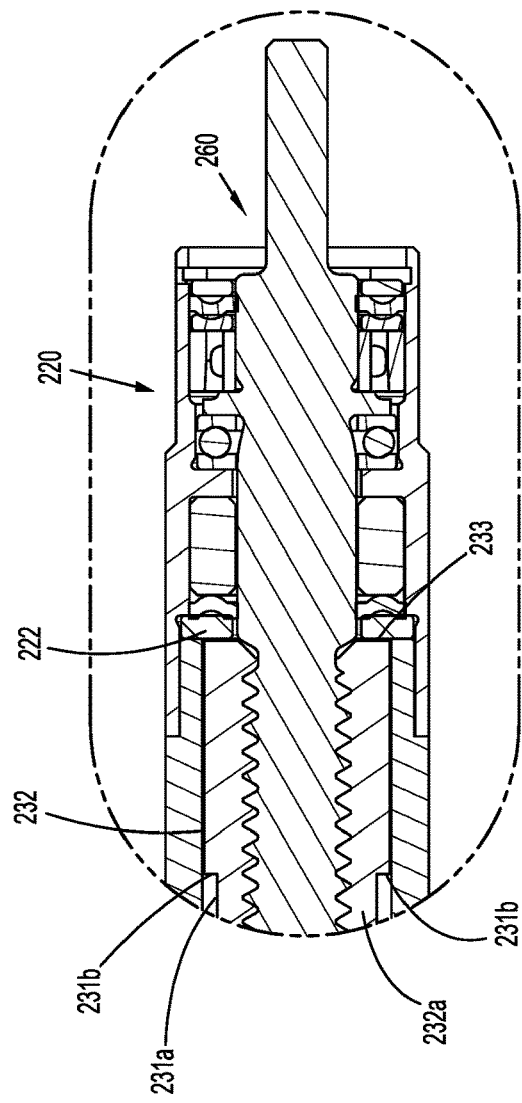

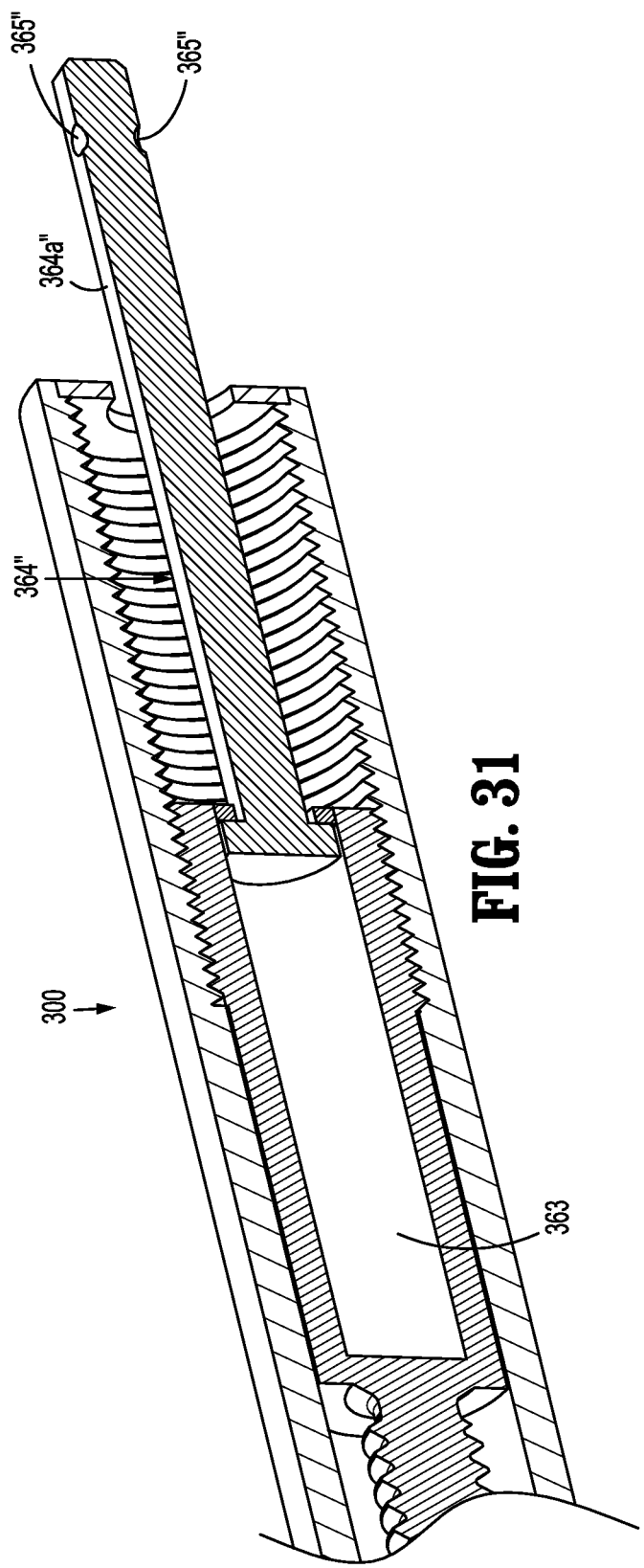
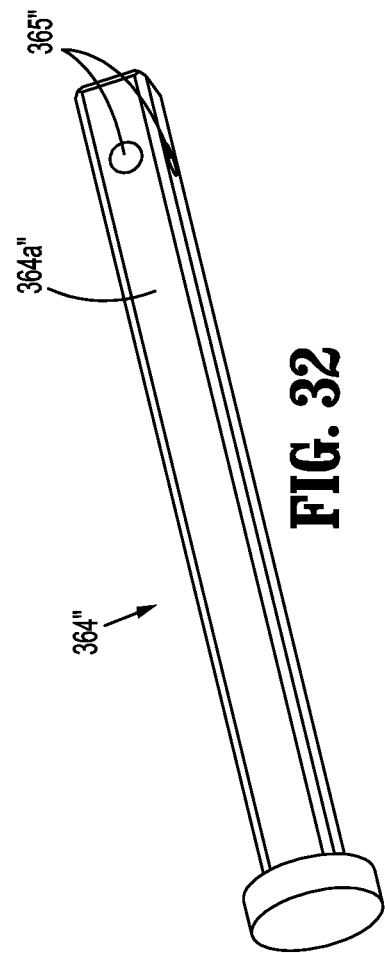
FIG. 31
FIG. 32

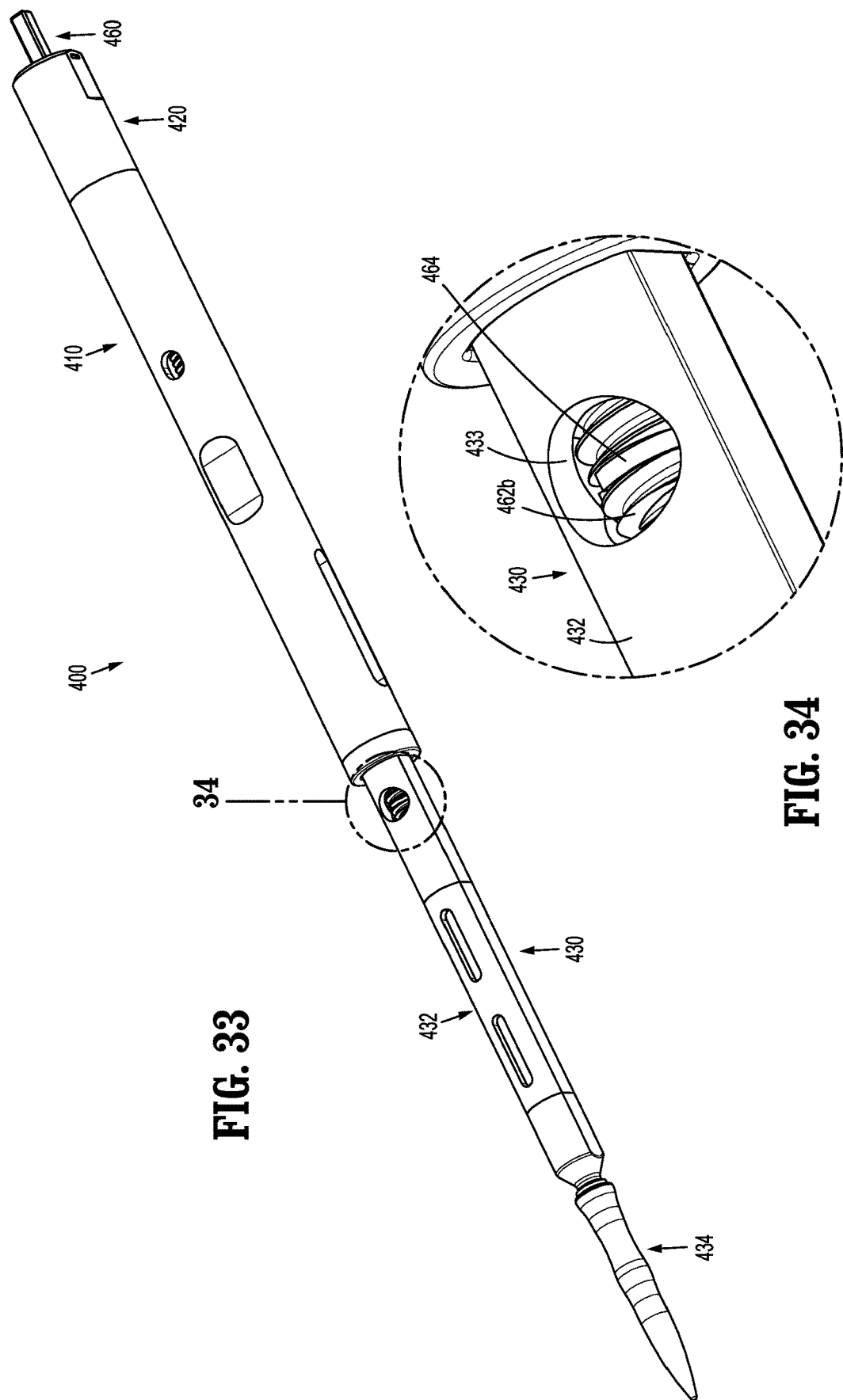

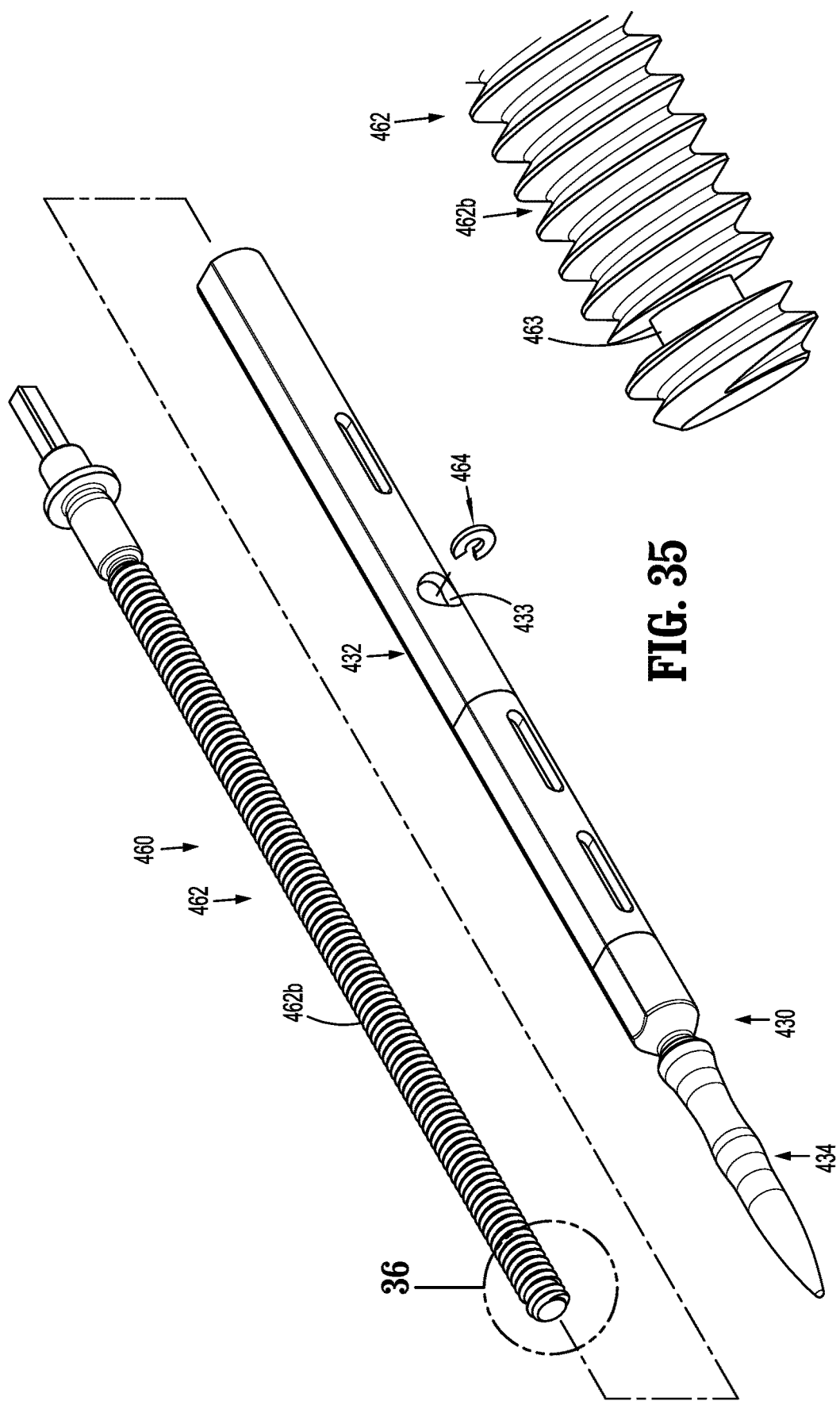

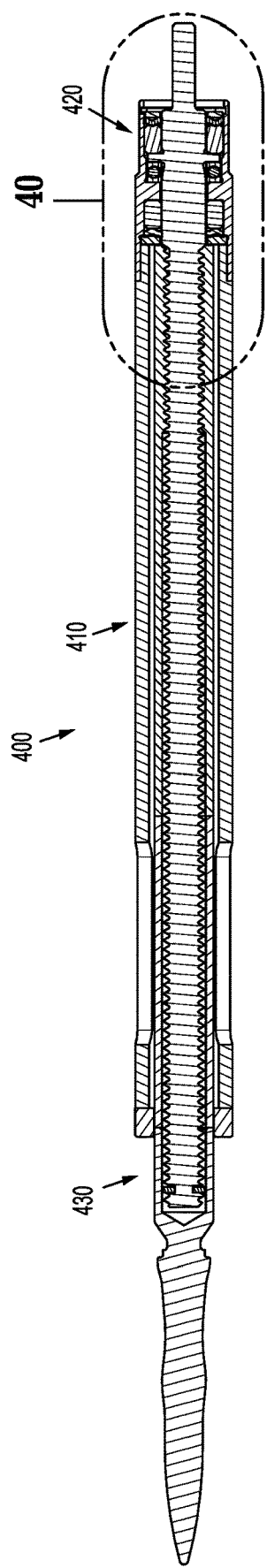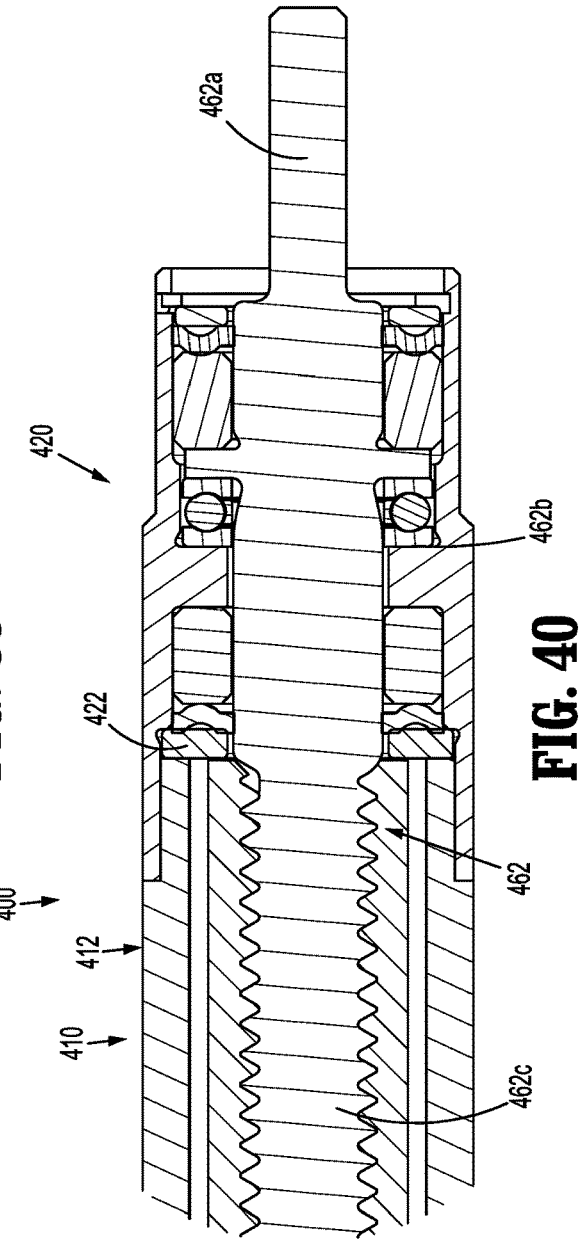
FIG. 39
FIG. 40

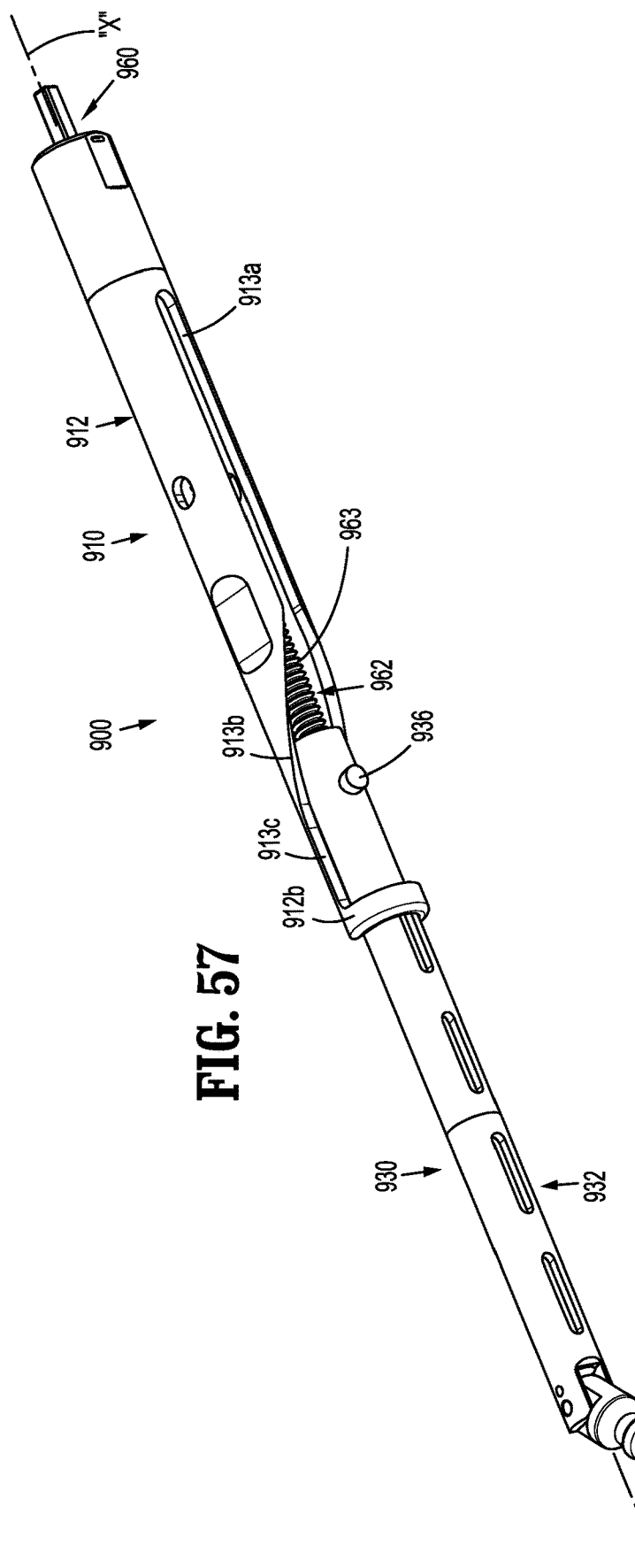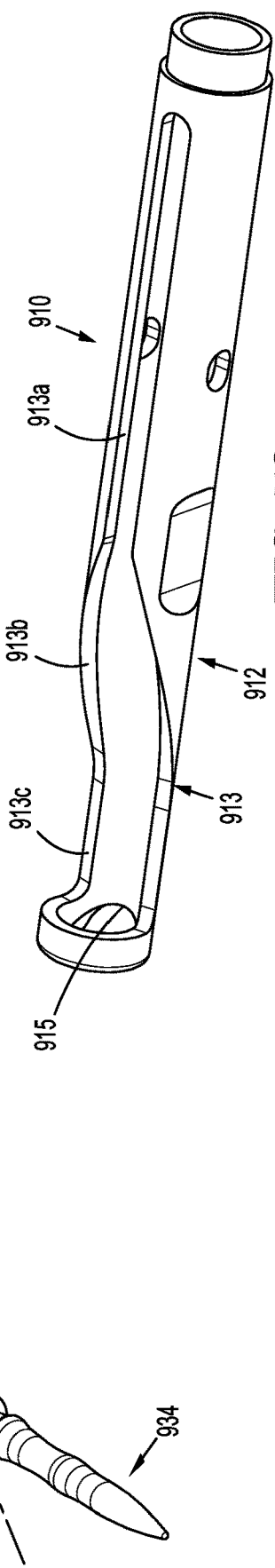

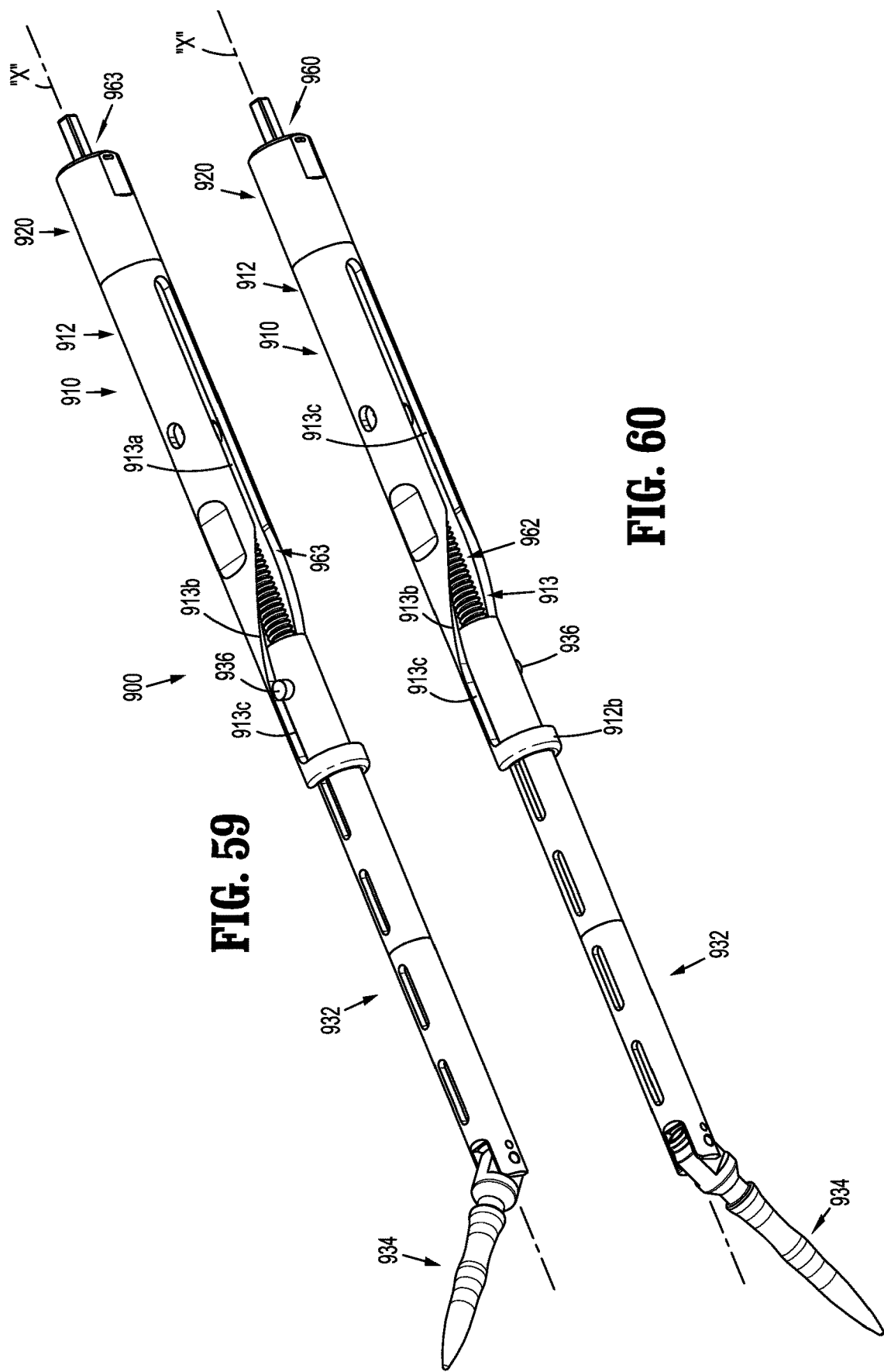

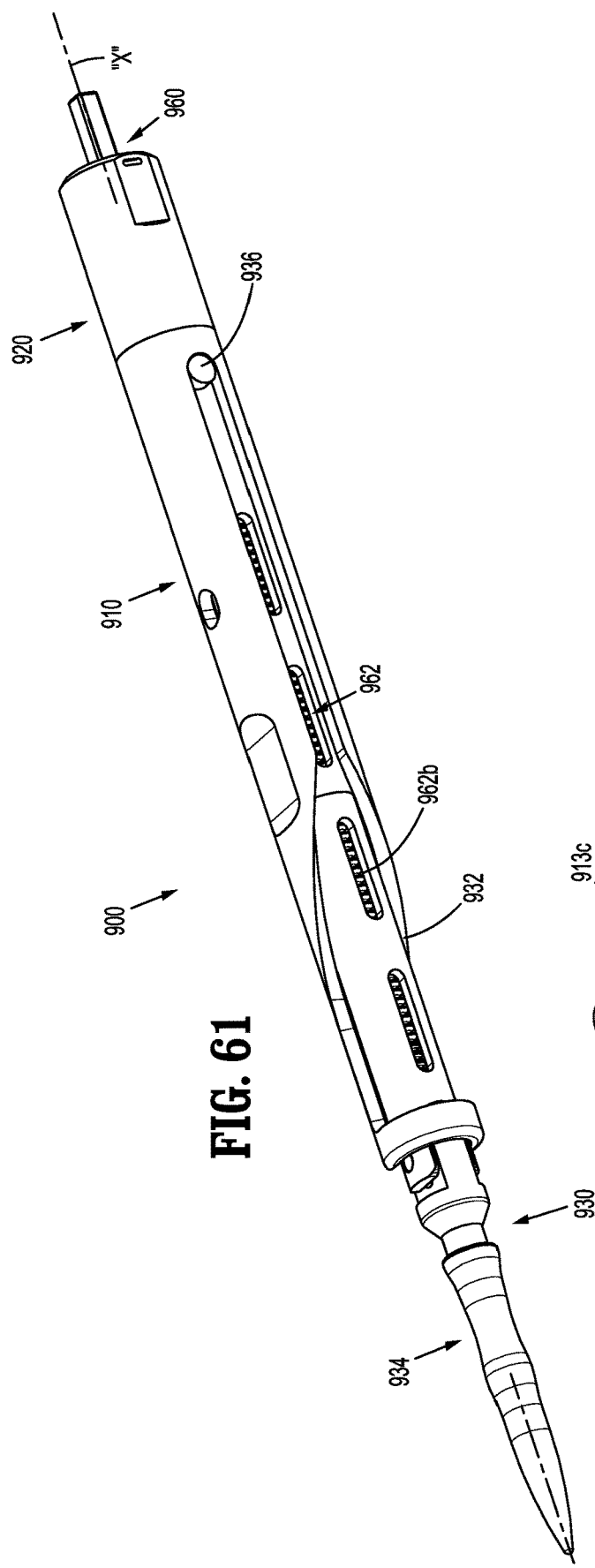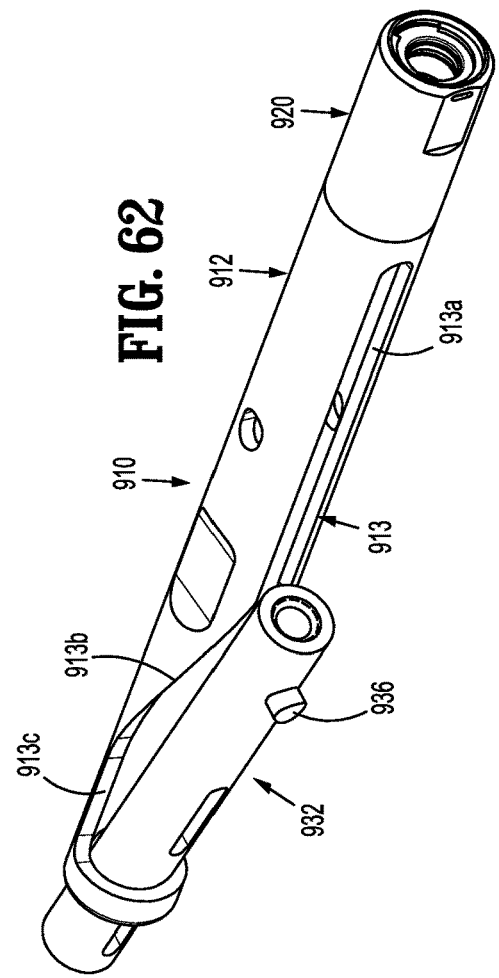

TROCAR ASSEMBLIES FOR ADAPTER ASSEMBLIES FOR SURGICAL STAPLING INSTRUMENTS

CROSS-REFERENCE TO RELATED APPLICATIONS

This application claims the benefit of, and priority to, U.S. Provisional Patent Application Nos. 62/834,490, 62/834,483; 62/834,493; 62/834,486; 62/834,502; each of which was filed on Apr. 16, 2019, the entire contents of each of which are incorporated herein by reference.

BACKGROUND

Technical Field

The present disclosure relates to circular stapling instruments. More particularly, the present disclosure relates to trocar assemblies for use in adapter assemblies for circular stapling instruments.

Background of Related Art

Surgical instruments for applying staples, clips, or other fasteners to tissue are well known. Typically, endoscopic stapling instruments include an actuation unit, e.g., a handle assembly for actuating the instrument, an elongate shaft for accessing a body cavity, and a tool assembly disposed at a distal end of the elongate shaft.

Adapter assemblies used with a circular stapling tool assembly include a trocar assembly for selectively positioning an anvil assembly relative to a cartridge assembly. To facilitate securing the anvil assembly relative to the cartridge assembly, it would be beneficial to have a trocar assembly with a trocar member that may be rotated and/or articulated.

SUMMARY

According to an aspect of the present disclosure, a trocar assembly for releasable engagement with an adapter assembly of a surgical stapling instrument, is provided. The trocar assembly includes a housing including a tubular body and defining a longitudinal axis, and a trocar mechanism supported with the housing and movable between a retracted position and an advanced position. The trocar mechanism includes a tubular member and a trocar member rotatably supported on a distal end of the tubular body such that the trocar member may be articulated through a plurality of angles in a plurality rotational orientations relative to the tubular body.

The trocar member may include a spherical proximal portion, and a distal portion of the tubular body defines a semi-spherical recess for receiving the spherical proximal portion of the trocar body.

The spherical proximal portion of the trocar member may be secured within the semi-spherical recess in the tubular body by a snap ring.

A bearing member may be received between the spherical proximal portion of the trocar member and the snap ring to facilitate articulation of the trocar member relative to the tubular member.

The spherical proximal portion of the trocar member may define a cylindrical recess.

The trocar mechanism may further include a lock member slidably disposed within the distal portion of the tubular member and movable between a locked or distal position and an unlocked or proximal position. The lock member may include a cylindrical body and a locking projection extending distally from the cylindrical body.

The locking projection of the lock member may be received within the cylindrical recess of the spherical proximal portion of the trocar member when the lock member is in a locked position, to fix the trocar member in longitudinal alignment with the longitudinal axis of the housing.

The spherical proximal portion of the trocar member may include a tapered surface about the cylindrical recess to facilitate receipt of the locking projection within the cylindrical recess.

A free end of the locking projection may include a tapered surface to facilitate receipt of the locking projection within the cylindrical recess of the trocar member.

The lock member may include a pair of tabs extending radially outwardly from the cylindrical body and the tubular body may define a pair of slots for receiving the pair of tabs of the lock member.

The lock member may be movable from the locked position to the unlocked position through engagement with the pair of tabs.

The trocar assembly may further include a drive member rotatably supported within the housing and configured to cause longitudinal translation of the trocar mechanism.

The drive member may be configured to engage the lock member as the trocar mechanism is moved to the retracted position to move the lock member to the locked position.

The trocar assembly may further include a bearing assembly disposed on a proximal end of the housing.

According to another aspect of the present disclosure, a trocar assembly for releasable engagement with an adapter assembly of a surgical stapling instrument is provided. The trocar assembly includes a housing including: a tubular body and defining a longitudinal axis; an end cap disposed on a distal end of the tubular body, the end cap including flattened inner surfaces; and a trocar member supported within the housing and received through end cap, the trocar member including flattened surfaces corresponding to the flattened inner surfaces of the end cap and stop surfaces disposed adjacent a proximal end of the flattened surfaces. The trocar member is movable between advanced and retracted positions and is rotationally fixed relative to the end cap through engagement of the flattener surfaces of the trocar member and the flattened inner surface of the end cap. The stop surface of the trocar member engages the end cap to prevent overextension of the trocar member from the housing.

According to a further aspect of the present disclosure, a trocar assembly for releasable engagement with an adapter assembly of a surgical stapling instrument is provided. The trocar assembly includes a housing including: a tubular body and defining a longitudinal axis, a proximal portion of the tubular body including a threaded inner surface; a trocar mechanism supported with the housing and movable between a retracted position and an advanced position, the trocar mechanism including a tubular member and a trocar member extending from the tubular member, the tubular member having a proximal section with a threaded inner surface; a drive member rotatably supported within the housing, the drive member including a threaded proximal portion configured for engagement with the threaded inner surface of the housing and a threaded distal portion configured for engagement with the threaded inner surface of the tubular member; and a drive connector in fixed rotational relationship and in dynamic longitudinal relationship with the drive member.

The drive connector may be maintained in a proximal position during advancement of the trocar mechanism by a plunger member and a spring.

The drive connector may include a seal member, and the drive connector may be biased in a proximal direction by a pressurized fluid.

The drive connector may include a detent for engaging a drive shaft of a handle assembly.

According to yet another embodiment of the present disclosure, a trocar assembly for releasable engagement with an adapter assembly of a surgical stapling instrument is provided. The trocar assembly includes: a housing including a tubular body and defining a longitudinal axis; a trocar member supported with the housing and movable between a retracted position and an advanced position, the trocar mechanism including a tubular member and a trocar member extending from the tubular member, the tubular member having a proximal section with a threaded inner surface; a drive member rotatably supported within the housing, the drive member including a threaded distal portion configured for engagement with the threaded inner surface of the tubular member, the threaded distal portion defining an annular groove; and a snap ring received within the annular groove, wherein during engagement of the threaded inner surface of the tubular member by the snap ring, the drive member is prevented from further rotation.

According to an aspect of the present disclosure, a trocar assembly for releasable engagement with an adapter assembly of a surgical stapling instrument is provided. The trocar assembly includes: a housing including a tubular body and defining a longitudinal axis, the tubular body defining at least one arcuate slot extending circumferentially about a distal portion of the tubular body; an end cap rotatably supported on the proximal portion of the tubular body, the end cap including at least one post configured to be received within the arcuate slot of the tubular body to limit rotation of the end cap; and a trocar mechanism supported with the housing and movable between a retracted position and an advanced position. The trocar mechanism includes a tubular member and a trocar member pivotally secured to the tubular member. The trocar mechanism and the end cap are rotationally fixed relative to one another such that rotation of the end cap along the longitudinal axis causes rotation of the trocar mechanism along the longitudinal axis.

According to another aspect of the present disclosure, a trocar assembly for releasable engagement with an adapter assembly of a surgical stapling instrument is provided. The trocar assembly includes: a housing including a tubular body and defining a longitudinal axis; an end cap supported on the proximal portion of the tubular body, the end cap defining a longitudinal passage and including at least a first nub extending radially into the longitudinal passage; and a trocar mechanism supported with the housing and movable between a retracted position and an advanced position. The trocar mechanism includes a tubular member and a trocar member pivotally secured to the tubular member. The tubular member defines at least one flattened portion corresponding to the at least first nub, wherein when the tubular member is received within the longitudinal passage of the end cap, the at least one nub aligns with the at least one flattened portion to permit rotation of the trocar mechanism along the longitudinal axis within the end cap.

According to a further aspect of the present disclosure, a trocar assembly for releasable engagement with an adapter assembly of a surgical stapling instrument is provided. The trocar assembly includes: a housing including a tubular body and defining a longitudinal axis, the tubular body defining a longitudinal slot having a narrow proximal portion and a wide narrow portion; and a trocar mechanism supported with the housing and movable between a retracted position and an advanced position. The trocar mechanism includes a tubular member and a trocar member pivotally secured to the tubular member. The trocar mechanism also includes a post extending radially outward from the tubular member, the post being receivable within the longitudinal slot in the housing, wherein the trocar mechanism is permitted to rotate about the longitudinal axis when the post is disposed within the wide distal portion of the longitudinal slot and the trocar mechanism is prevented from rotating when the post is disposed within the narrow proximal portion of the longitudinal slot.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 4 is a perspective view of a housing assembly and a trocar mechanism of the trocar assembly shown in FIG. 3;

FIG. 5 is an exploded perspective view of the trocar mechanism shown in FIG. 4;

FIG. 14 is a perspective view of the trocar assembly shown in FIG. 3, with the trocar mechanism in an advanced position;

FIG. 15 is a cross-sectional side view taken along line 15-15 shown in FIG. 14;

FIG. 16 is a perspective view of a trocar assembly according to another embodiment of the present disclosure, with a trocar mechanism in an advanced position;

FIG. 17 is a cross-sectional side view taken along line 17-17 shown in FIG. 16;

FIG. 20 is a cross-sectional view as shown in FIG. 17, with the trocar mechanism in a retracted position;

FIG. 21 is an enlarged view of the indicated area of detail shown in FIG. 20;

FIG. 31 is an enlarged cross-sectional perspective view of a proximal portion of a drive assembly according to another embodiment of the present disclosure;

FIG. 32 is a perspective side view of a drive connector of the drive assembly shown in FIG. 31;

FIG. 33 is a perspective side view of a trocar assembly according to yet another embodiment of the present disclosure;

FIG. 34 is an enlarged view of the indicated area of detail shown in FIG. 33;

FIG. 35 is a perspective side view of a trocar mechanism and a drive member of the trocar assembly shown in FIG. 33;

FIG. 36 is an enlarged view of the indicated area of detail shown in FIG. 36;

FIG. 39 is a cross-sectional view as shown in FIG. 36, with the trocar mechanism in a retracted position;

FIG. 40 is an enlarged view of the indicated area of detail shown in FIG. 39;

FIG. 57 is a perspective side view of a trocar assembly according to yet another embodiment of the present disclosure;

FIG. 58 is a perspective side view of a housing assembly of the trocar assembly shown in FIG. 57;

FIG. 59 is a perspective side view of the trocar assembly shown in FIG. 57, with a trocar mechanism in a first rotational orientation;

FIG. 60 is a perspective side view of the trocar assembly shown in FIG. 57, with the trocar mechanism in a second rotational orientation;

FIG. 61 is a perspective side view of the trocar assembly shown in FIG. 57, with the trocar mechanism in a retracted position; and FIG. 62 is a perspective end view of the housing assembly and a proximal end of the trocar mechanism of the trocar assembly shown in FIG. 57, as the trocar mechanism is secured to the housing assembly.

DETAILED DESCRIPTION

Figure 1:
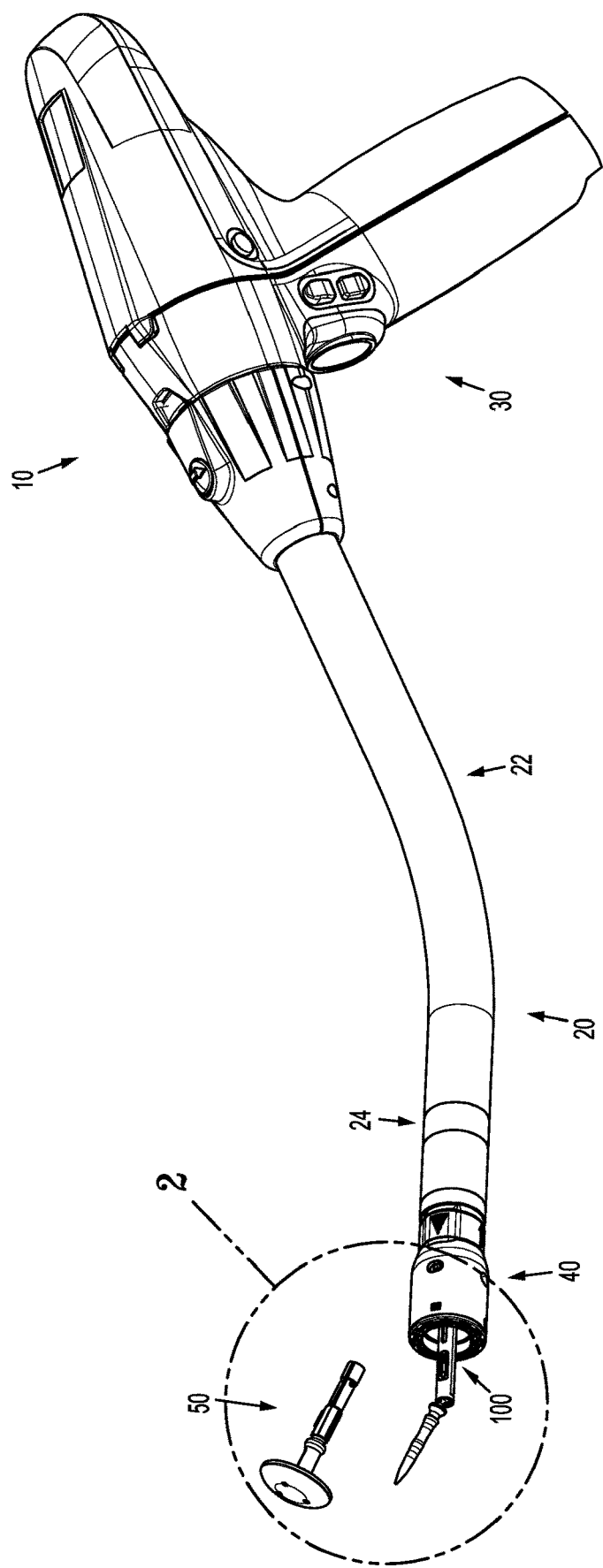
FIG. 1 is a perspective view of a surgical stapling instrument including a trocar assembly according to an embodiment of the present disclosure.

Embodiments of the presently disclosed trocar assemblies will now be described in detail with reference to the drawings in which like reference numerals designate identical or corresponding elements in each of the several views. As is common in the art, the term "proximal" refers to that part or component closer to the user or operator, e.g. surgeon or clinician, while the term "distal" refers to that part or component farther away from the user.

Referring initially to FIG. 1, an adapter assembly suitable for use with a removable trocar assembly according to an embodiment of the present disclosure, shown generally as adapter assembly 20, is a component of a surgical stapling instrument 10. The surgical stapling instrument 10 further includes a powered handle assembly 30, a loading unit 40, and an anvil assembly 50. Although shown and described with reference to surgical stapling instrument 10, the aspects of the present disclosure may be modified for use with surgical stapling instruments having alternative configurations. For a detailed description of exemplary powered surgical stapling instruments, please refer to commonly owned U.S. Pat. Nos. 9,023,014 and 9,055,943 ("the '014 patent" and "the '943 patent", respectively), the contents of each of which are incorporated by reference herein in their entirety.

The adapter assembly 20 of the surgical stapling instrument 10 will only be described to the extent necessary to fully disclose the aspects of the present disclosure. For a detailed description of exemplary adapter assemblies, please refer to commonly owned U.S. Pat. App. Pub. Nos. 2016/0106406 ("the '406 publication") and 2017/0086879 ("the '879 publication"), the contents of each of which are incorporated by reference herein in their entirety.

With continued reference to FIG. 1, the adapter assembly 20 includes a proximal portion 22 configured for operable connection to the handle assembly 30 (FIG. 1) and a distal portion 24 configured for operable connection to the loading unit 40 (FIG. 1). Although shown and described as forming an integral unit, it is envisioned that the proximal and distal portions 22, 24 may be formed as separate units that are releasably securable to one another.

Figure 3:
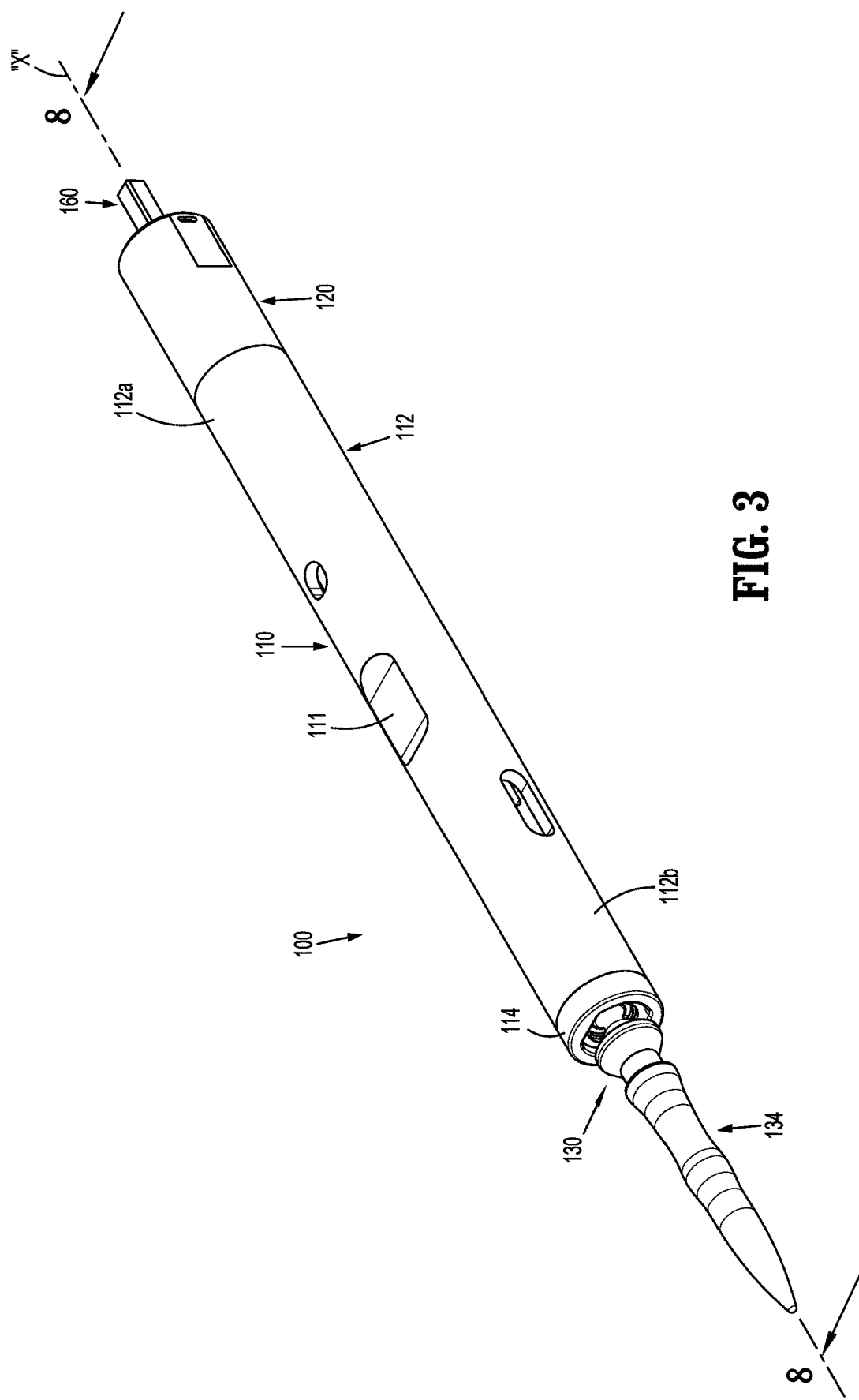
FIG. 3 is a perspective view of the trocar assembly of the adapter assembly shown in FIG. 1.

With additional reference to FIG. 3, a removable trocar assembly according to an embodiment of the present disclosure, shown generally as trocar assembly 100, extends distally from the distal portion 24 of the adapter assembly 20 of the surgical stapling instrument 10. The trocar assembly 100 is releasably secured within the distal portion 24 (FIG. 1) of the adapter assembly 20. For a detailed description of an exemplary locking mechanism for securing the trocar assembly 100 within the distal portion 24 of the adapter assembly 20, please refer to the '879 publication, the content of which was previously incorporated by reference herein.

Figure 2:
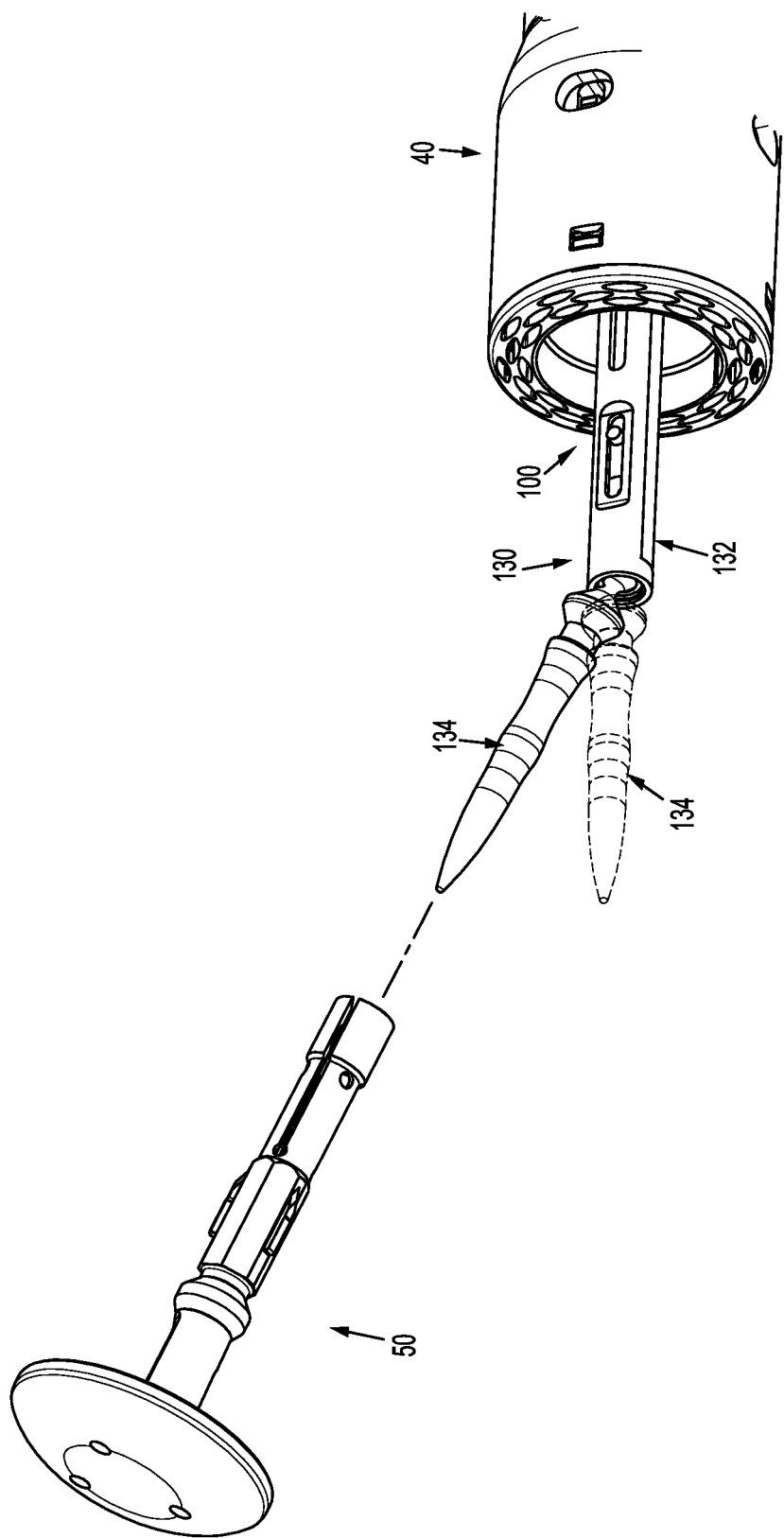
FIG. 2 is a perspective view of a distal end of the surgical stapling instrument shown in FIG. 1, including a loading unit, a trocar assembly, and an anvil assembly.

With reference now to FIGS. 3-7, the trocar assembly 100 of the adapter assembly 20 (FIG. 2) of the surgical stapling instrument 10 includes a housing assembly 110, a bearing assembly 120 supported on a proximal end of the housing assembly 110, a trocar mechanism 130 slidably disposed within and extending from the housing 110, and a drive member 160 rotatably supported within the housing assembly 110 by the bearing assembly 120 for longitudinally moving the trocar mechanism 130 relative to the housing assembly 110.

The housing assembly 110 of the trocar assembly 100 includes a tubular body 112 having proximal and distal portions 112a, 112b. In embodiments, the tubular body 112 defines a pair of notches 111 to facilitate releasable attachment of the trocar assembly 100 within the distal portion 24 (FIG. 1) of the adapter assembly 20 of the surgical stapling instrument 10. Alternatively, the tubular body 112 of the housing assembly 110 may include tabs, slots and tabs, threading, or other suitable configuration for releasable attachment of the trocar assembly 100 to the adapter assembly 20. An end cap 114 is disposed on the distal portion 112b of the tubular body 112. The bearing assembly 120 of the trocar assembly 100 is disposed on the proximal portion 112a of the tubular body 112. The bearing assembly 120 and/or the end cap 114 may be secured to the tubular body 112 using adhesive, welding, friction fit, mechanical interface, e.g., threads or bayonet coupling, or in any other suitable manner.

The bearing assembly 120 of the trocar assembly 130 is configured to rotatably support the drive member 160. An exemplary bearing assembly is shown and described in the '406 publication, the content of which was previously incorporated by reference herein.

With particular reference now to FIGS. 4-10, the trocar mechanism 130 of the trocar assembly 100 is configured for longitudinal movement relative to the housing assembly 110 of the trocar assembly 100. The trocar mechanism 130 includes a tubular member 132 slidably disposed within the housing assembly 110, a trocar member 134 extending distally from within the tubular member 132, and an articulation mechanism 140 operably disposed within the tubular member 132 and configured to permit selective articulation of the trocar member 134 relative to the tubular member 132.

The tubular member 132 of the trocar mechanism 130 includes a proximal section 132a and a distal section 132b. The proximal and distal sections 132a, 132b, may be secured together in any suitable manner, including with adhesive, welding, mechanical fasteners or the like. In embodiments, the proximal and distal sections 132a, 132b of the tubular member 132 are integrally formed. An inner surface 133a (FIG. 8) of the proximal section 132a of the tubular member 132 is threaded. The threaded inner surface 133a is configured to engage a threaded portion 162c of the drive member 160. The distal section 132b of the tubular member 132 is configured to operably retain and support a proximal end of the trocar member 134 and the articulation mechanism 140. More particularly, the distal section 132b of the tubular member 132 defines a semispherical recess 131a for receiving a spherical portion 134a of the trocar member 134 and slots 131b (FIG. 10) for receiving tab portions 152 extending outwardly from the lock member 142 of the articulation mechanism 140.

Figure 7:
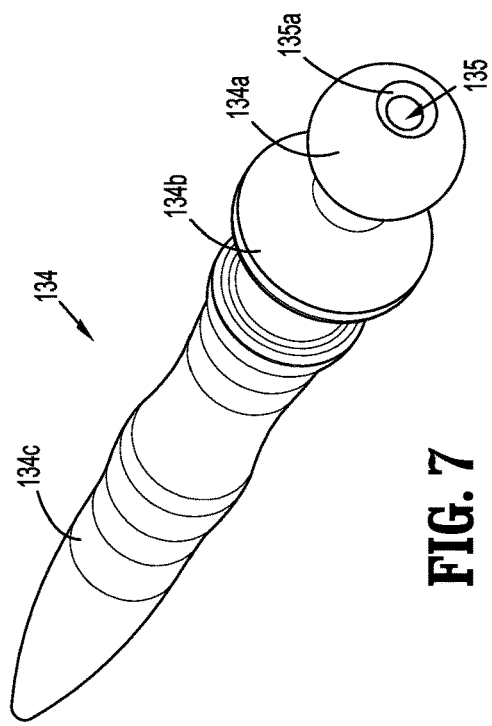
FIG. 7 is a perspective end view of a trocar member of the trocar assembly shown in FIG. 3.
Figure 6:
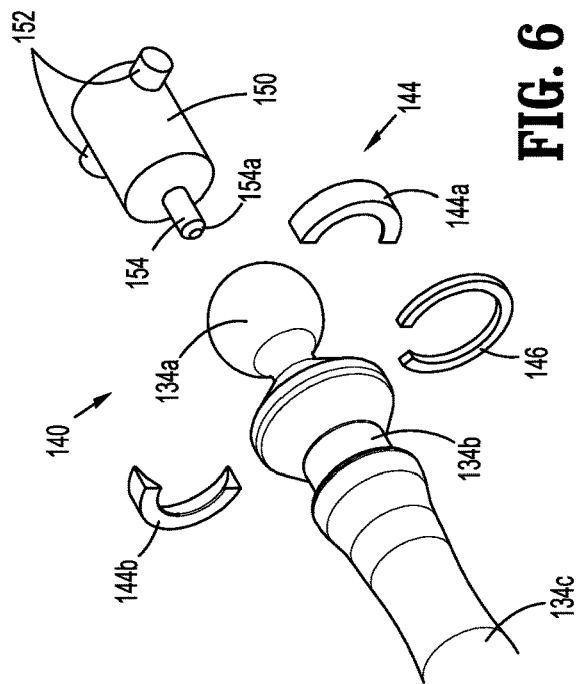
FIG. 6 is an exploded perspective view of an articulation assembly of the trocar mechanism shown in FIG. 4.

With particular reference to FIG. 7, the trocar member 134 includes the spherical portion 134a, a flanged or intermediate portion 134b, and a tapered or distal portion 134c. The spherical portion 134a of the trocar member 134 is configured to be received within the semispherical recess 131a in the distal section 132b of the tubular member 132 of the trocar mechanism 130. The spherical portion 134a defines a cylindrical recess 135 (FIG. 8) extending along a longitudinal axis "x" of the trocar member 134. As will be described in further detail below, the cylindrical recess 135 in the spherical portion 134a of the trocar member 134 receives a locking projection 154 of the lock member 142 of the articulation mechanism 140 to orient and secure the trocar member 134 in a longitudinally aligned configuration. The spherical portion 134a of the trocar member 134 includes a tapered surface 135a (FIG. 8) formed about an entrance to the cylindrical recess 135 to facilitate receipt of the locking projection 154 of the lock member 142 within the cylindrical recess 135a. The flanged intermediate portion 134b of the trocar member 134 is configured for operable engagement with an anvil assembly, e.g., the anvil assembly 50 (FIG. 1). The tapered distal portion 134c of the trocar member 134 is configured for piercing tissue and for facilitating engagement of the trocar member 134 with the anvil assembly 50.

With particular reference now to FIGS. 5-10, the articulation mechanism 140 of the trocar mechanism 130 includes the lock member 142, a bearing member 144, and a snap ring 146. As shown, the bearing member 144 includes first and second bearing halves 144a, 144b, although other configurations are envisioned. The bearing member 144 of the articulation mechanism 140 rotatably supports the spherical portion 134a of the trocar member 134 within semispherical recess 131a in the distal section 132b of the tubular member 132, and is operably retained within the semispherical recess 131a by the snap ring 146.

Figure 13:
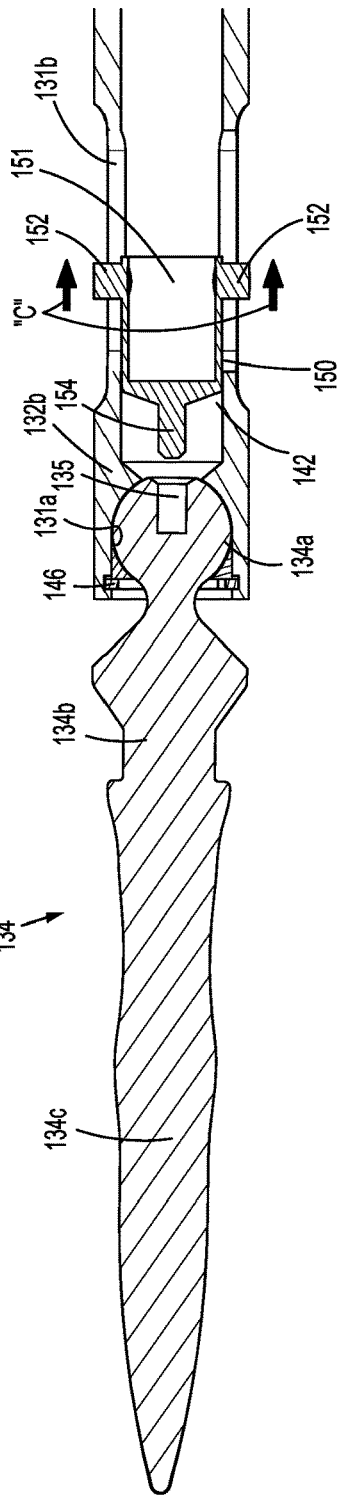
FIG. 13 is an enlarged view as shown in FIG. 12, with a lock member in a retracted position.
Figure 18:
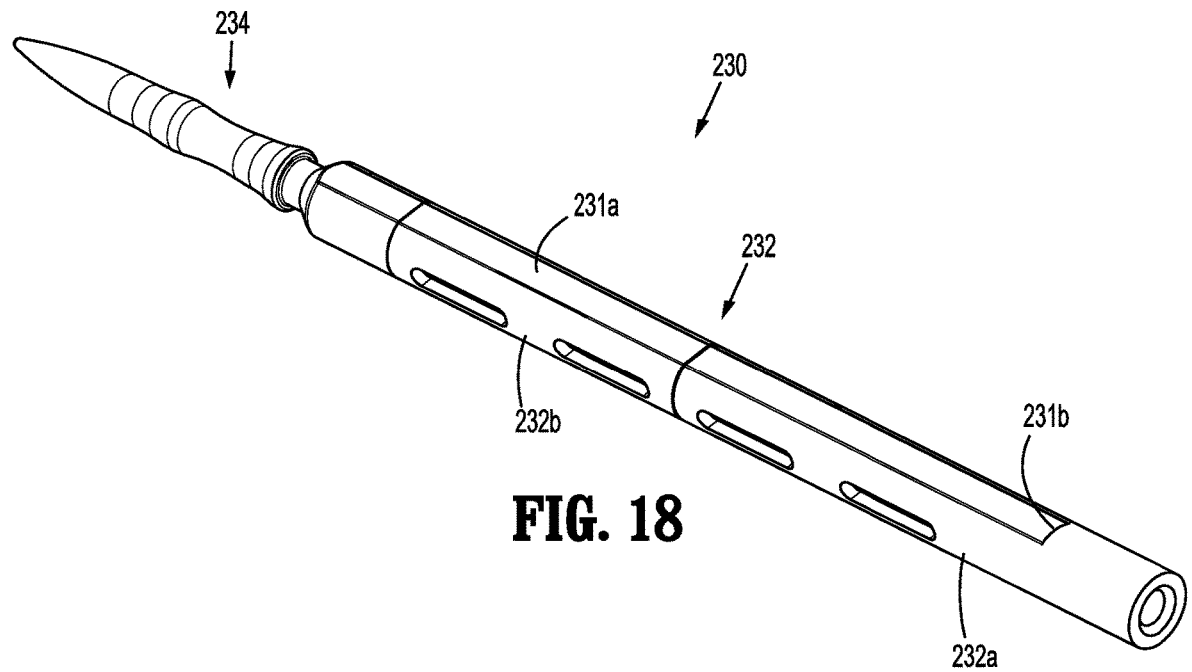
FIG. 18 is a perspective view of the trocar mechanism shown in FIG. 16.

The lock member 142 of the articulation mechanism 140 of the trocar assembly 100 is slidably disposed within the distal section 132b of the tubular member 132. The lock member 142 includes a substantially cylindrical body 150, the tab portions 152 extending radially outwardly from the cylindrical body 150, and a locking projection 154 extending distally from the cylindrical body 150. The cylindrical body 150 defines a recess 151 for receiving a distal end of the drive member 160. The tab portions 152 are received within in the slots 131b in the distal section 132b of the tubular member 132 of the trocar mechanism 130, and permit longitudinal movement of the lock member 142 between a locked or initial position (FIG. 9) and an unlocked or retracted position (FIG. 13). The locking projection 154 includes a tapered free end 154a configured to facilitate receipt of the locking projection 154 within the cylindrical recess 135 of the spherical portion 134a of the trocar member 134.

The drive member 160 of the trocar assembly 100 includes an elongate body 162 having a proximal or engagement portion 162a, an intermediate bearing portion 162b, and a threaded or distal portion 162c. The proximal engagement portion 162a of the drive member 160 is configured for operable engagement with a drive screw (not shown) disposed within the adapter assembly 20. The bearing portion 162b of the drive member 160 rotatably engages the bearing assembly 120 to permit rotation of the elongate body 162 about its longitudinal axis. The threaded portion 162c operably engages the inner threaded portion 133a of the proximal section 132a of the tubular member 132 to cause longitudinal movement of the trocar mechanism 130 relative to the housing assembly 110.

Figure 8:
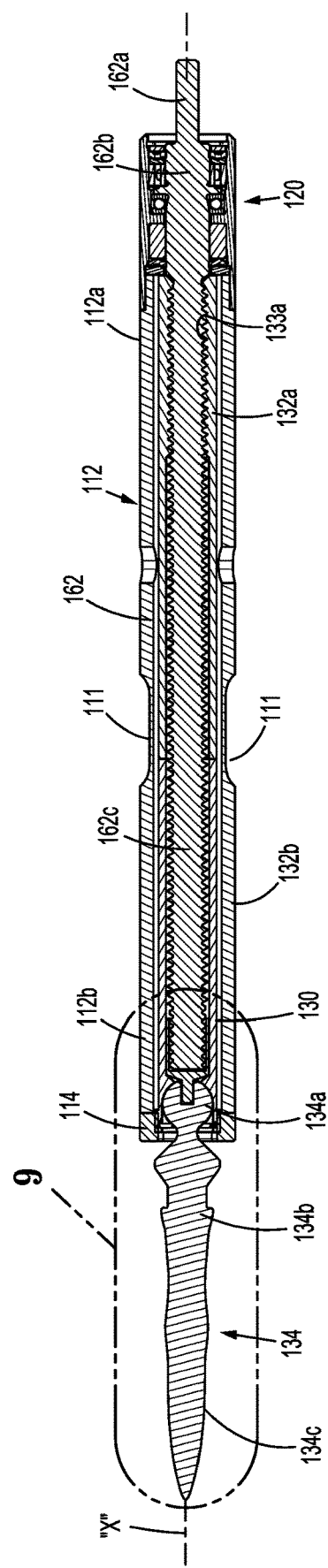
FIG. 8 is a cross-sectional side view taken along line 8-8 shown in FIG. 4.
Figure 9:
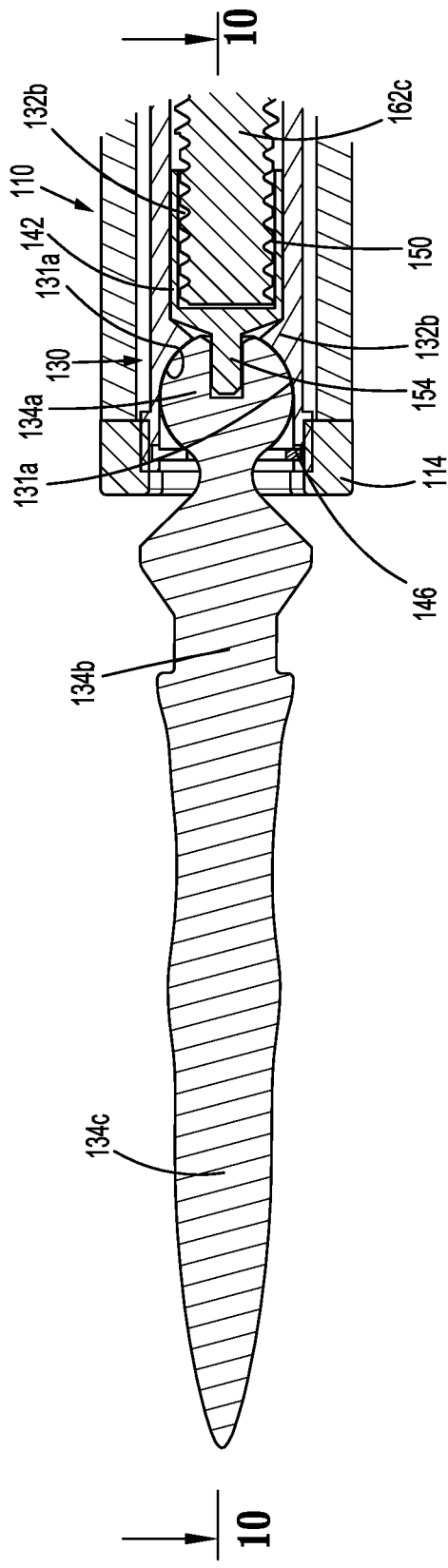
FIG. 9 is an enlarged view of the indicated area of detail shown in FIG. 8.
Figure 10:
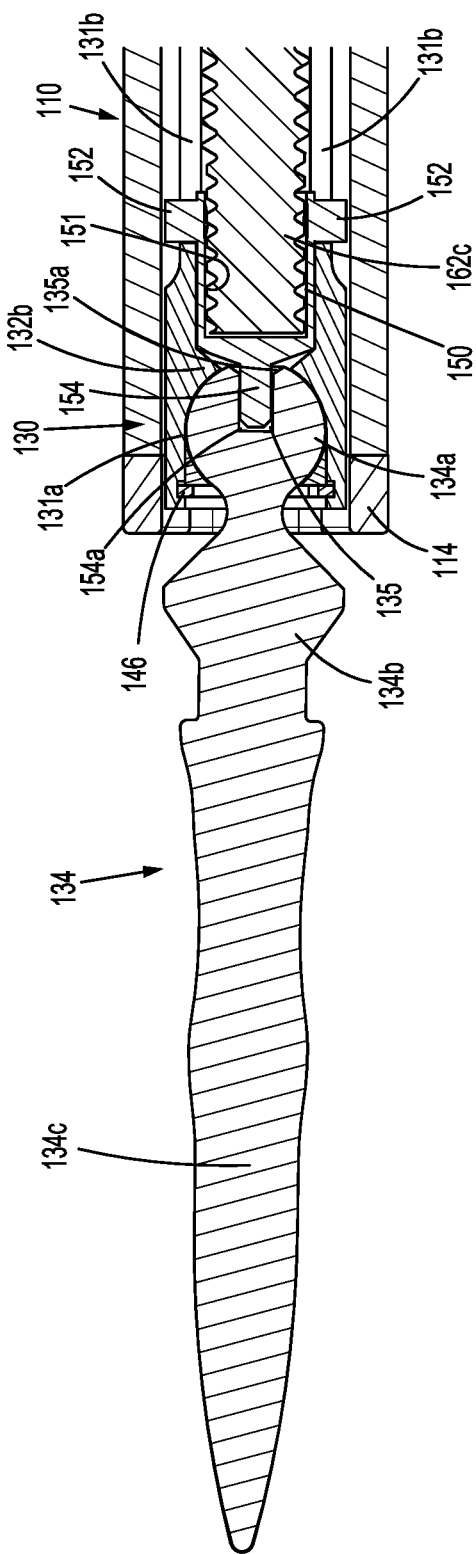
FIG. 10 is a cross-sectional top view taken along line 10-10 shown in FIG. 9.

The operation of the trocar assembly 100 will now be described with reference to FIGS. 8-15. Referring initially to FIGS. 8-10, whether provided to the clinician with the trocar assembly 100 preloaded within the adapter assembly 20 (FIG. 1), or provided to the clinician separate from the adapter assembly 20 and, therefore, requiring loading within the adapter assembly 20, the trocar assembly 100 is provided to the clinician with the trocar mechanism 130 in a retracted position and the lock member 142 of the articulation mechanism 140 in a locked position. When the trocar mechanism 130 is in the retracted position, a distal end of the drive member 160 is received within the recess 151 formed in the cylindrical body 150 of the lock member 142. When the lock member 142 of the articulation mechanism 140 is in the locked position, the trocar member 134 is fixed in longitudinal alignment with the elongate body 162 of the drive member 160. When in the longitudinally fixed position, the trocar member 134 may be used in a traditional manner, e.g., to pierce tissue.

Figure 12:
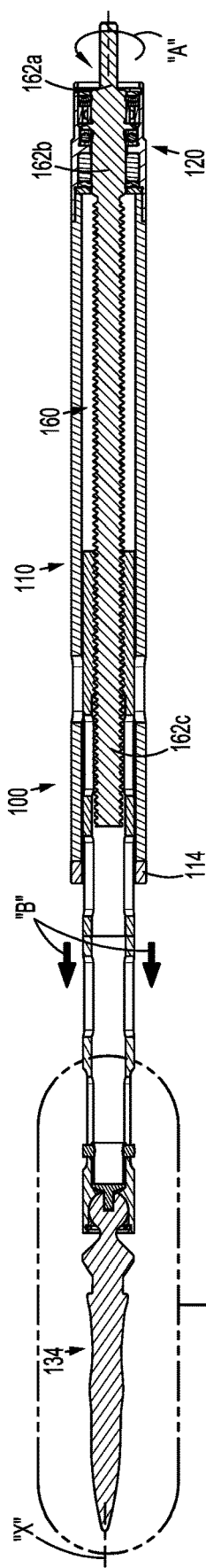
FIG. 12 is an enlarged view of the indicated area of detail shown in FIG. 11.
Figure 11:
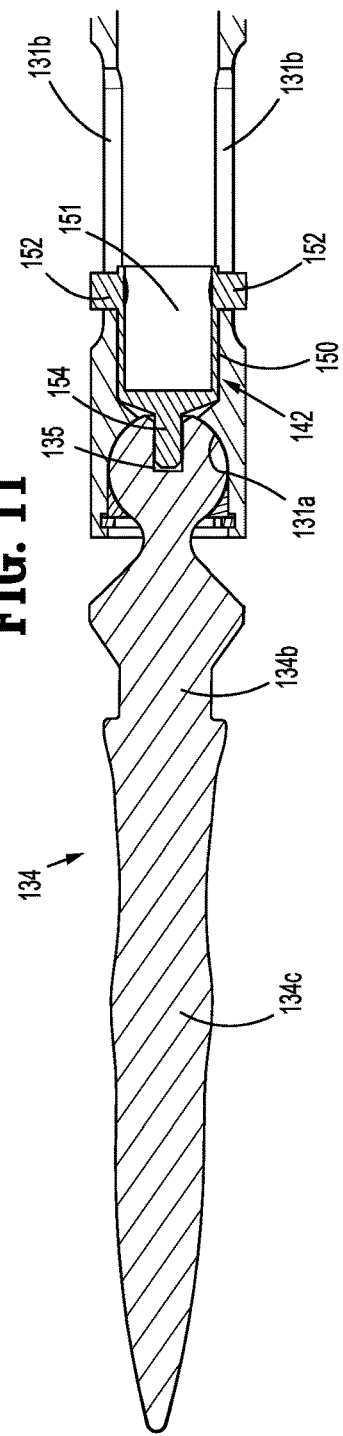
FIG. 11 is a cross-sectional view as shown in FIG. 8, with the trocar mechanism in an advanced position.

Turning to FIGS. 11 and 12, rotation of the drive member 160 in a first direction, as indicted by arrow "A" in FIG. 11, causes the trocar member 134 to move distally, e.g., advance, as indicated by arrows "B" in FIG. 11. During advancement of the trocar member 134, the lock member 142 remains in the locked position with the locking projection 154 received within the cylindrical opening 135 in the spherical portion 134a of the trocar member 134. In this manner, the trocar member 134 remains in longitudinal alignment with the elongate body 162 of the drive member 160. In embodiments, the lock member 142 may be keyed to the drive member 160 such that retraction of the drive member 160 causes retraction of the lock member 142. In this manner, retraction of the drive member 160 would disengage the lock member 142 from the trocar member 134, thereby permitting articulation of the trocar member 134 relative to the housing assembly 110. Alternatively, the locking projection 154 may be formed directly on the drive member 162.

Turning to FIGS. 13-16, to disengage the lock member 142 from the trocar member 134, the clinician engages the tabs 142a of the lock member 142 through slots 131b in the distal section 132b of the tubular member 132 of the trocar mechanism 130 and moves the lock member 142 in a proximal direction, e.g., retracts, as indicated by arrows "C" in FIG. 13, to an unlocked position. Proximal movement of the lock member 142 withdraws the locking projection 154 of the lock member 142 from within the cylindrical opening 135 in the spherical portion 132a of the trocar member 132.

When the lock member 142 of the articulation mechanism 140 is in the unlocked position, the trocar member 134 is free to articulate in any direction relative to the end cap 114 of the housing assembly 110. In this manner, the trocar member 134 may be oriented at any angle relative to the housing assembly 110 (FIGS. 2 and 14), to facilitate attachment of the anvil assembly 50 (FIG. 2) to the trocar member 134.

Subsequent to attaching the anvil assembly 50 to the trocar member 134, the trocar member 134 is retracted by rotating the drive member 160 in a second, opposite direction. As the trocar member 134 is retracted within the housing assembly 110 of the trocar assembly 100, the trocar member 134 engages the end cap 114 of the housing assembly 110 to cause the trocar member 134 to realign with the elongate body 162 of the drive member 160. Continued retraction of the trocar member 134 causes the distal end 162b of the elongate body 162 of the drive member 160 to engage the lock member 142. As the trocar member 134 continues to retract, the locking projection 154 of the lock member 142 engages the spherical portion 134a of the trocar member 134. The tapered surface 135a surrounding an open end of the cylindrical recess 135 in the spherical portion 134a of the trocar member 134 and the tapered free end 154a of the locking projection 154 facilitate receipt of the locking portion 144 of the lock member 142 within the cylindrical recess 135.

As described above, receipt of the locking projection 154 of the lock member 152 within the cylindrical recess 135 in the spherical portion 134a of the trocar member 134 fixes the trocar member 134 in longitudinal alignment with the elongate body 162 of the drive member 160. The surgical stapling instrument 10 (FIG. 1) may then be used to complete the stapling procedure in a traditional manner.

With reference now to FIGS. 16-21, a trocar assembly according to another embodiment of the present disclosure is shown generally as trocar assembly 200. The trocar assembly 200 is substantially similar to the trocar assembly 100 described hereinabove, and will only be described in detail as it relates to the differences therebetween.

The trocar assembly 200 includes a housing assembly 210, a bearing assembly 220 supported on a proximal end of the housing assembly 210, a trocar mechanism 230 slidably disposed within the housing assembly 210, and a drive member 260 rotatably supported within the housing assembly 210 by the bearing assembly 220 for longitudinally moving the trocar mechanism 230 relative to the housing assembly 210.

Figure 19:
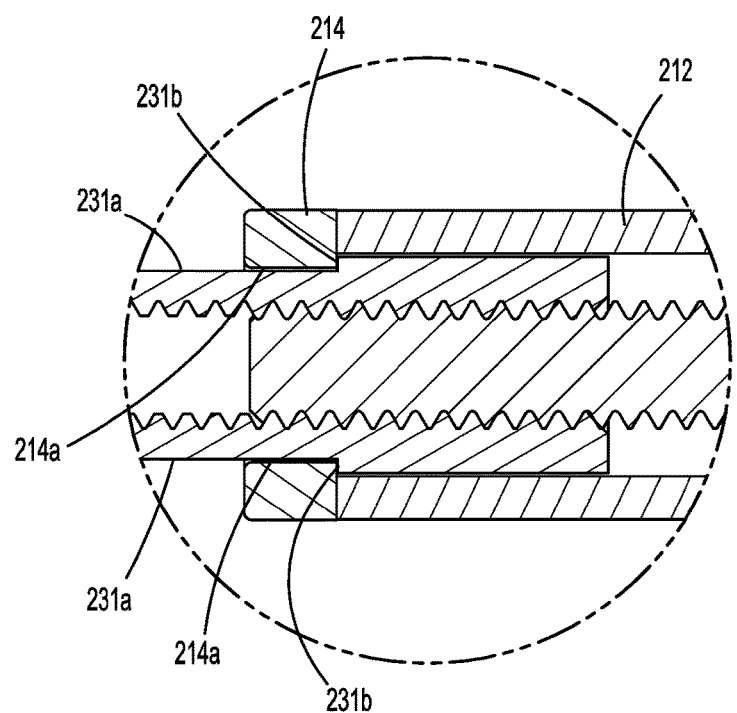
FIG. 19 is an enlarged view of the indicated area of detail shown in FIG. 17.
Figure 22:
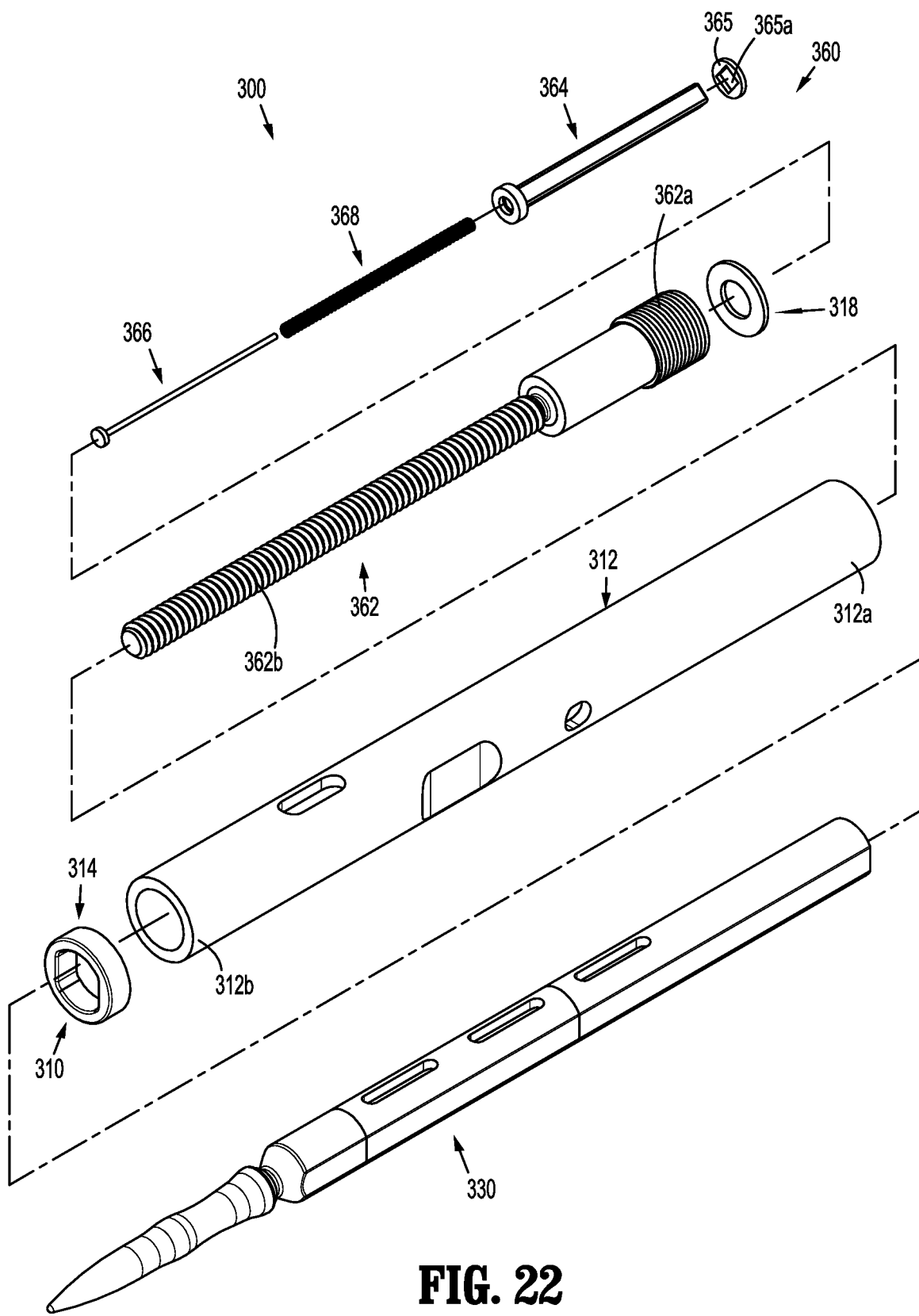
FIG. 22 is an exploded perspective view of a trocar assembly according to another embodiment of the present disclosure.

The trocar mechanism 230 of the trocar assembly 200 is configured for longitudinal movement relative to the housing assembly 210 of the trocar assembly 200. The trocar mechanism 230 is secured within a tubular body 212 of housing assembly 210 by an end cap 214. The end cap 214 includes flattened inner surfaces 214a (FIG. 19). The trocar mechanism 230 includes a tubular member 232 slidably disposed within the housing assembly 210 and a trocar member 234 secured to and extending distally from the tubular member 232.

As shown, the tubular member 232 of the trocar mechanism 230 includes proximal and distal sections 232a, 232b. It is envisioned that the tubular member 232 may be monolithic. The tubular member 232 includes elongate flattened surfaces 231a extending along opposed lengths of the tubular member 232 and a stop surface 231b (FIG. 19) disposed adjacent the proximal ends of the elongate flattened surfaces 231a. The elongate flattened surfaces 231a of the tubular member 232 of the trocar mechanism 230 align with flattened inner surfaces 214a of the end cap 214 of a housing assembly 210 to maintain the trocar member 232 in a fixed rotational orientation relative to the housing assembly 210.

With particular reference to FIG. 19, the stop surface 231b of the tubular member 232 of the trocar mechanism 230 engages the end cap 214 of the housing assembly 210 during longitudinal movement of the trocar mechanism 230 relative to the housing assembly 210, e.g., advancement. Engagement of the stop surfaces 231b of the tubular member 232 with the end cap 214 retains the trocar mechanism 230 within the housing assembly 210 and prevents over extension of the trocar member 234 from the housing assembly 210.

With particular reference to FIG. 21, a proximal facing surface 233 of the tubular member 232 of the trocar assembly 200 is configured to engage a stop member 222 disposed between the tubular body 212 of the housing assembly 210 and the bearing assembly 220 of the housing assembly 210. In embodiments, the stop member 222 includes a snap ring. The stop member 222 limits the proximal movement of the trocar mechanism 230 to prevent over-retraction of the trocar mechanism 230 within the housing assembly 210.

With reference now to FIGS. 22-28, a trocar assembly according to another embodiment of the present disclosure is shown generally as trocar assembly 300. The trocar assembly 300 is substantially similar to the trocar assemblies 100, 200 described hereinabove, and will only be described in detail as it relates to the differences therebetween.

The trocar assembly 300 includes a housing assembly 310, a trocar mechanism 330 slidably disposed within the housing 310, and a drive assembly 360 rotatably supported within the housing assembly 310 for longitudinally moving the trocar mechanism 330 relative to the housing assembly 310.

Figure 24:
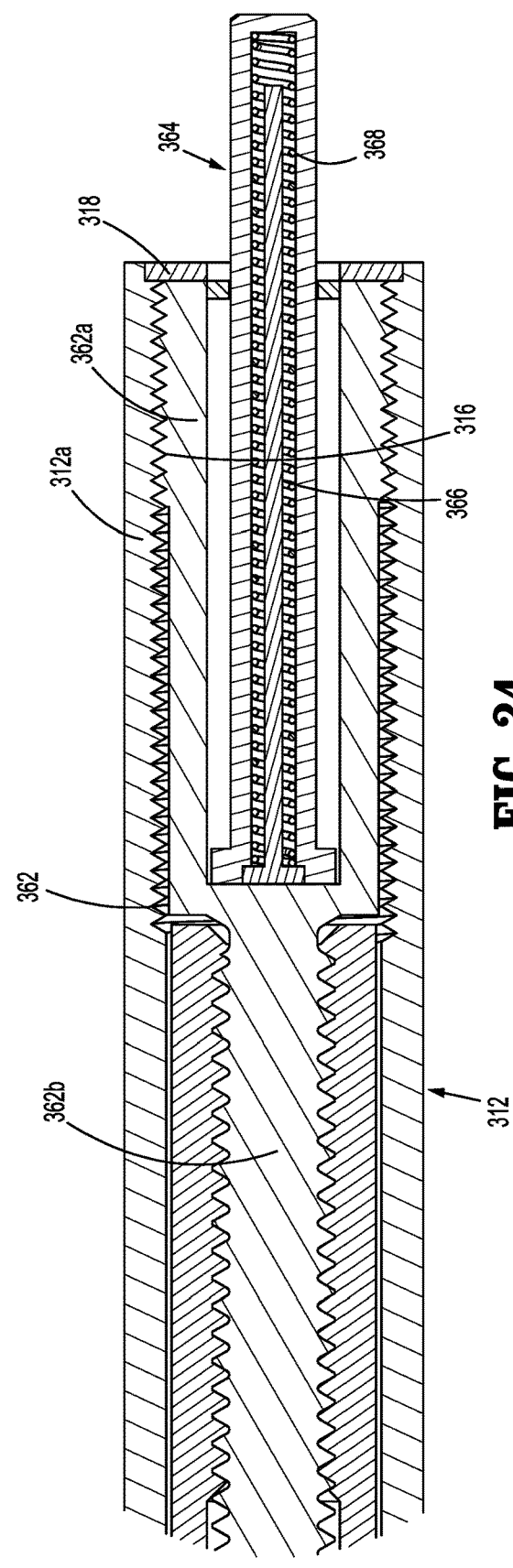
FIG. 24 is an enlarged view of the indicated area of detail shown in FIG. 23.

The housing assembly 310 of the trocar assembly 300 includes a tubular body 312 and an end cap 314 disposed on a distal portion 312b of the tubular body 312. A proximal portion 312a of the tubular body 312 includes a threaded inner surface 316 (FIG. 24). As will be described in further detail below, the threaded inner surface 316 of the tubular body 312 engages a threaded proximal portion 362a of the drive member 362 of the drive assembly 360 to cause longitudinal translation of the drive member 362 relative to the housing assembly 310.

The trocar mechanism 330 of the trocar assembly 300 is configured for longitudinal movement relative to the housing assembly 310 of the trocar assembly 300. The trocar mechanism 330 is secured within a tubular body 312 of housing assembly 310 by the end cap 314 on the distal portion 312b of the tubular body 312 and the drive assembly 360 on the proximal portion 312a of the tubular body 312. The trocar mechanism 330 includes a tubular member 332 slidably disposed within the housing assembly 310 and a trocar member 334 secured to and extending distally from the tubular member 332.

The drive assembly 360 of the trocar assembly 300 includes the drive member 362, a drive connector 364 extending from a threaded proximal portion 362a of the drive member 362, a plunger member 366 slidably disposed within the drive connector 364, and a spring member 368 biasing the plunger member 366. The plunger member 366 and the spring member 368 operate to maintain the drive connector 364 in a proximal position, e.g., in engagement with a drive shaft (not shown) within the adapter assembly 20 (FIG. 1).

The drive member 362 of the drive assembly 360 includes the threaded proximal portion 362a and a threaded distal portion 362b. The threaded proximal portion 362a is threaded in a first direction and the threaded distal portion 362b is threaded in a second direction. As noted above, the threaded proximal portion 362a of the drive member 362 is configured to engage the threaded inner surface 316 of the tubular body 312 of the housing assembly 310. Rotation of the drive connector 364 causes longitudinal movement of the drive member 362 relative to the housing assembly 310. The threaded distal portion 362b of the drive member 362 engages a threaded inner surface 333 of a proximal portion 332a of the tubular member 332. Rotation of the drive member 362 causes longitudinal movement of the trocar mechanism 330 relative to the housing assembly 310.

A pitch of the threaded proximal portion 362a of the drive member 362 may be the same or different from a pitch of the threaded distal portion 362b. By varying the pitch of the threaded proximal and distal portions 362a, 362b of the drive member 362, the rate at which the respective drive member 362 and the trocar mechanism 330 move in the longitudinal direction may be varied. In embodiments, the threaded distal portion 362b of the drive member 362 is more coarse (e.g., relatively larger thread pitch) to move the trocar mechanism 330 further while the threaded proximal portion 362a is more fine (e.g., relatively smaller thread pitch) for use in both displacing and axial retaining the drive member 362 to the tubular body 312 of the housing assembly 310.

The threaded proximal portion 362a of the drive member 362 of the drive assembly 360 defines a cylindrical recess 363 for receiving the drive connector 364, the plunger member 366, and the spring member 368. A washer 365 defines a rectangular opening 365a (FIG. 22) is welded or otherwise fixedly secured to the threaded proximal portion 362a of the drive member 362 within the cylindrical recess 363 to maintain a flanged distal end 364a of the drive connector 364 within the cylindrical recess 363 and to rotationally fix the plunger member 366 relative to the drive member 362. More particularly, a proximal portion 364a of the drive connector 364 includes a rectangular profile that is slidingly received through rectangular opening 365a of the washer 365. In this manner, rotation of the drive connector 364 causes rotation of the drive member 362.

As noted above, the plunger member 364 includes the proximal portion 364a that includes a rectangular profile and a distal portion 364b that is flanged. The rectangular profile of the proximal portion 364a rotationally fixes the drive connector 364 relative to the drive member 362 and the flange of the distal portion 364b retains the drive connector 364 within the cylindrical recess 363 of the drive member 362. The drive connector 364 defines a longitudinal cavity 367 for receiving the spring member 368 received about the plunger member 366. The spring member 366 is maintained about the plunger member 366 by a flanged distal portion 366b of the plunger member 366. The spring member 368 is configured to bias the plunger member 366 distally, or more particularly, to bias the drive connector 364 proximally. The plunger member 366 and the spring member 368 operate to maintain the drive connector 364 in a proximal position to ensure engagement of the drive connector 364 with a drive shaft (not shown) of the adapter assembly 20 (FIG. 1).

Figure 23:
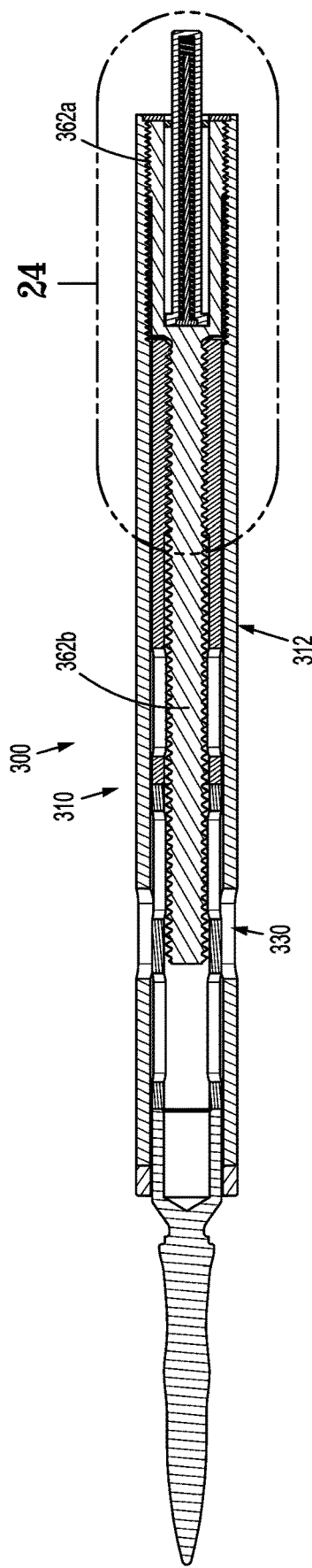
FIG. 23 is a cross-sectional side view of the trocar assembly shown in FIG. 22.

With particular reference to FIGS. 23 and 24, the trocar mechanism 330 of the trocar assembly 300 is shown in a retracted or distal position. When in the retracted position, the trocar mechanism 330 is disposed adjacent a distal end of the threaded proximal portion 362*a* of the drive member 362 and a proximal end of the threaded proximal portion 362*a* of the drive member 362 engages a washer 318 secured within the proximal end of the tubular body 312 of the housing assembly 310 to retain the drive member 362 within the tubular body 312, and to act as a stop for the drive member 312 to prevent over-retraction of the drive member 312 within the housing assembly 310.

Figure 25:
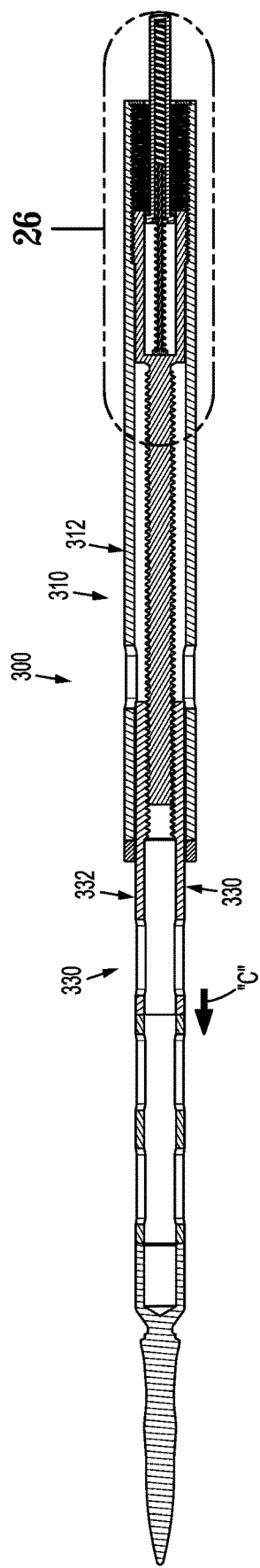
FIG. 25 is a cross-sectional view as shown in FIG. 23, with the trocar mechanism in an advanced position.
Figure 26:
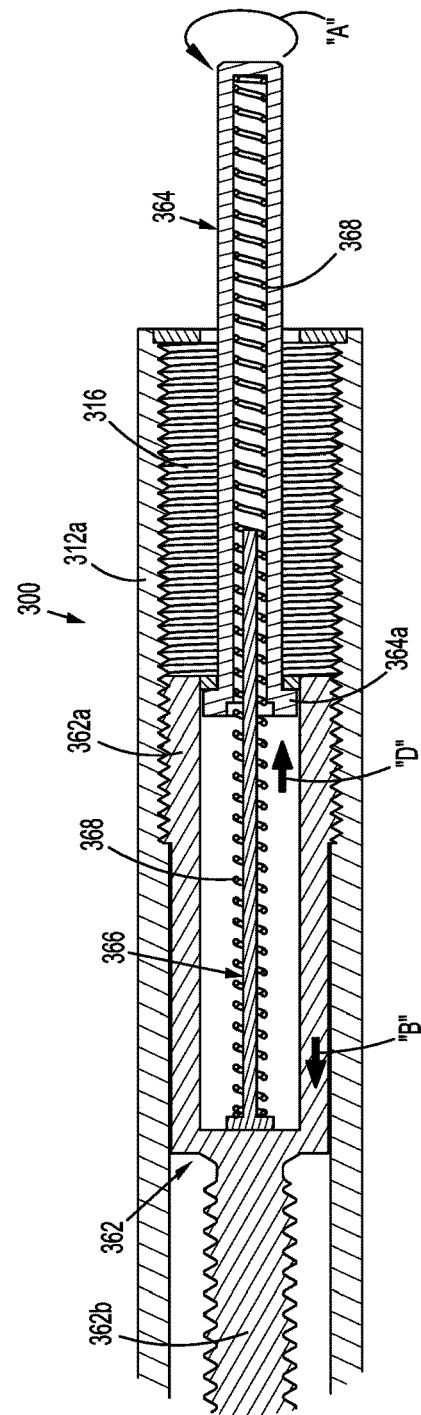
FIG. 26 is an enlarged view of the indicated area of detail shown in FIG. 25.
Figure 27:
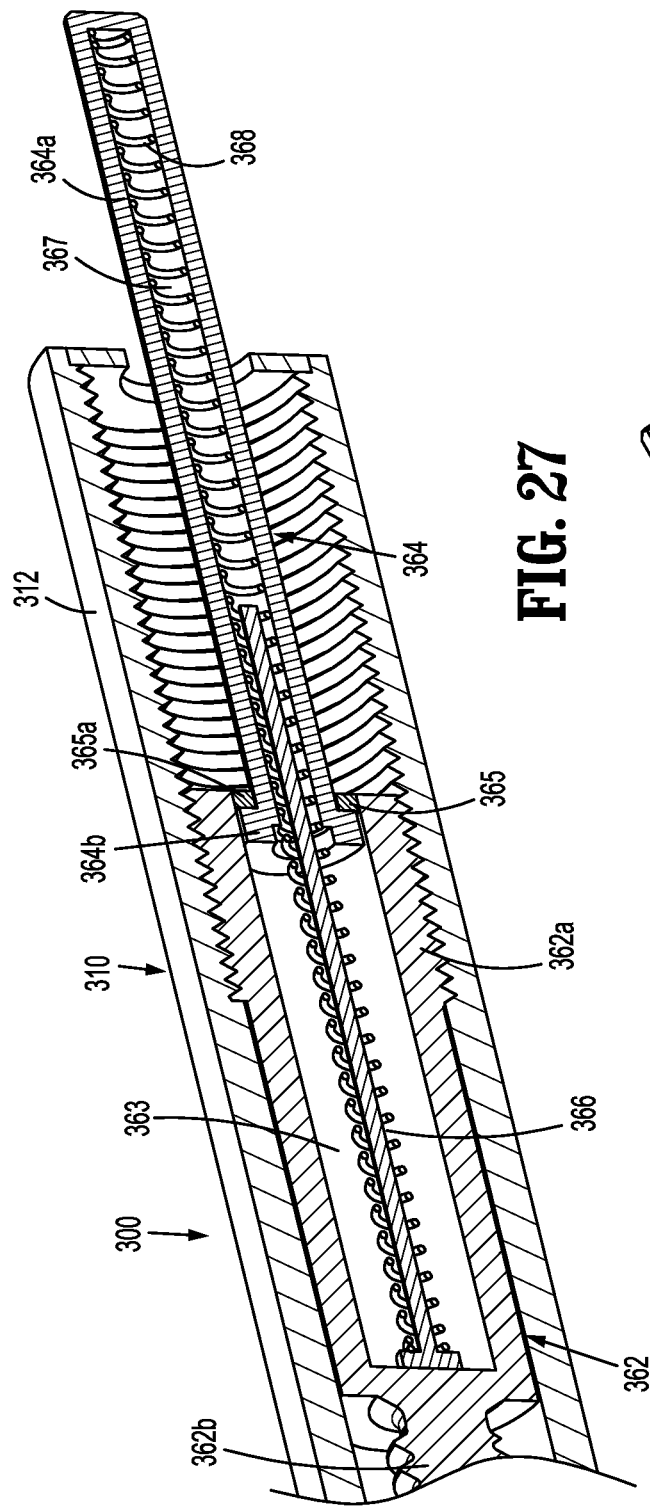
FIG. 27 is an enlarged cross-sectional perspective view of a proximal portion of the trocar assembly shown in FIG. 22.
Figure 28:
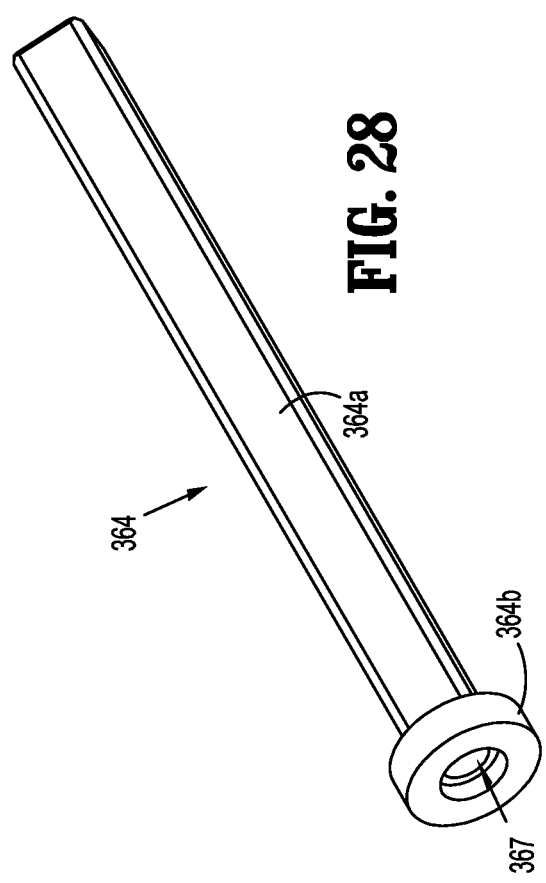
FIG. 28 is a perspective side view of a drive connector of a drive mechanism of the trocar assembly shown in FIG. 22.

Turning to FIGS. 25 and 26, rotation of the drive connector 364 of the drive assembly 360 in a first direction, as indicated by arrow "A" in FIG. 26, causes corresponding rotation of the drive member 362 in the same, first direction. Rotation of the drive member 362 causes longitudinal movement of the drive member 362 in a distal direction, e.g., advancement, as indicated by arrow "B" in FIG. 26. Rotation of the drive member 362 in the first direction also causes longitudinal movement of the trocar mechanism 330 in a distal direction, as indicated by arrow "C" in FIG. 25. As the drive member 362 moves distally within the housing assembly 310, the spring member 368 of the drive assembly 360 biases the drive connector 364 proximally to maintain the drive connector 364 in the proximal position in engagement with the drive shaft (not shown) of the adapter assembly 20 (FIG. 1).

The trocar mechanism 330 is returned to the retracted position by rotating the drive connection in a second, opposite direction.

Figure 29:
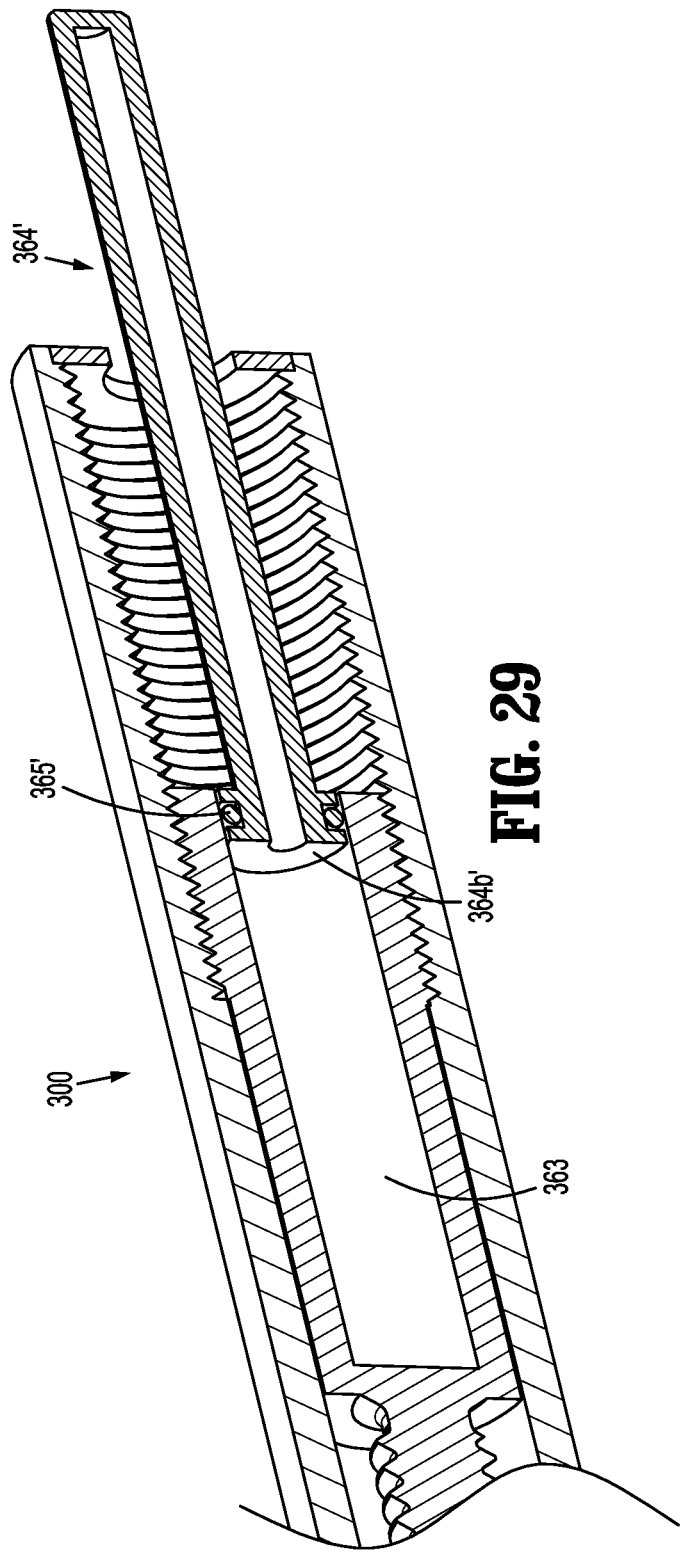
FIG. 29 is an enlarged cross-sectional perspective view of a proximal portion of a drive assembly according to another embodiment of the present disclosure.
Figure 30:
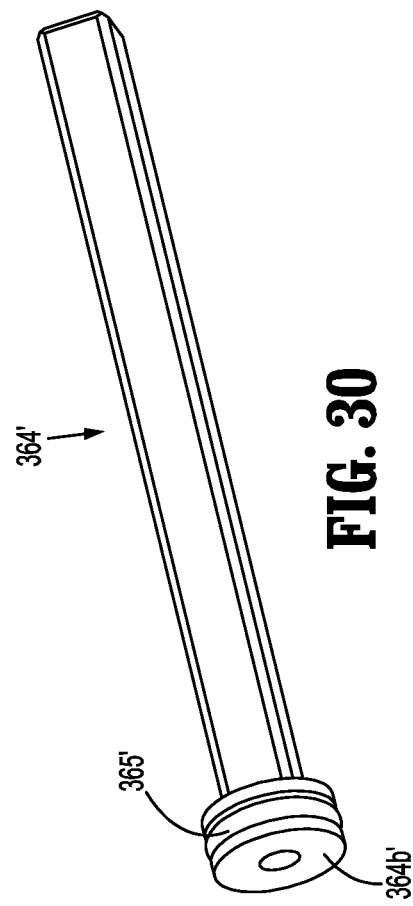
FIG. 30 is a perspective side view of a drive connector of the drive assembly shown in FIG. 29.

With reference to FIGS. 29 and 30, in another embodiment of trocar assembly 300, the drive connector 364, the plunger member 366, and the spring member 368 are replaced by a single piston member 364'. The piston member 364' includes a flanged distal portion 364*b*' having a seal member 365' received thereabout. The seal member 365' creates a fluid tight seal between the flanged distal portion 364*b*' of the piston member 364' and the drive member 362. A pressurized fluid received within the cylindrical recess 363 of the drive member 362 biases the piston member 364' proximally during longitudinal movement of the drive member 362 to maintain the piston member 364' in contact with the drive shaft (not shown) of the adapter assembly 20 (FIG. 1).

With reference to FIGS. 31 and 32, in another embodiment of trocar assembly 300, the plunger member 366 and the spring member 368 are replaced by a drive connector 364" having detents 365" on a proximal portion 364*a*" of the drive connector 364". The detent 365" engages the drive shaft (not shown) of the adapter assembly 20 (FIG. 1) to maintain engagement of the drive connector 364" with the drive shaft. Although shown including more than one detent 365", it is envisioned that the proximal portion 364*a*" of the drive connector 364" may include only one detent 365". It is further envisioned that the drive connector 364" may be secured to the drive shaft in other suitable manners, e.g., friction fit, bayonet coupling, mechanical fasteners.

With reference now to FIGS. 33-40, a trocar assembly according to another embodiment of the present disclosure is shown generally as trocar assembly 400. The trocar assembly 400 is substantially similar to the trocar assemblies 100, 200, 300 described hereinabove, and will only be described in detail as it relates to the differences therebetween.

The trocar assembly 400 includes a housing assembly 410, a bearing assembly 420 supported on a proximal end of the housing assembly 410, a trocar mechanism 430 disposed within the housing 410, and a drive member 460 rotatably supported within the housing assembly 410 by the bearing assembly 420 for longitudinally moving the trocar assembly 430 relative to the housing assembly 410.

The trocar mechanism 430 of the trocar assembly 400 is configured for longitudinal movement relative to the housing assembly 410 of the trocar assembly 400. The trocar mechanism 430 includes a tubular member 432 slidably disposed within the housing assembly 410 and a trocar member 434 extending distally from the tubular member 432. The tubular member 432 defines an opening 433 that provides access to a distal portion 462*a* of an elongate body 462 of the drive member 460. The tubular member 432 includes a threaded inner surface 436 (FIG. 38) that engages a threaded distal portion 462*b* of the drive member 462.

The drive member 460 includes the elongate body 462 including a proximal portion 462*a* and the threaded distal portion 462*b*. The threaded distal portion 462*b* of the elongate body 462 is configured to engage a snap ring 464. More particularly, the distal portion 462*b* of the elongate body 462 defines a groove 463 for receiving the snap ring 464. Although shown including a snap ring 464, it is envisioned that the distal portion 462*b* of the elongate body 462 may instead be configured to receive a pin, cap or nut that may be bonded, welded, staked or otherwise secured to the drive member 462. Alternatively, the threads of the distal portion 462*b* of the elongate body 462 of the drive member 460 may be deformed.

Figure 37:
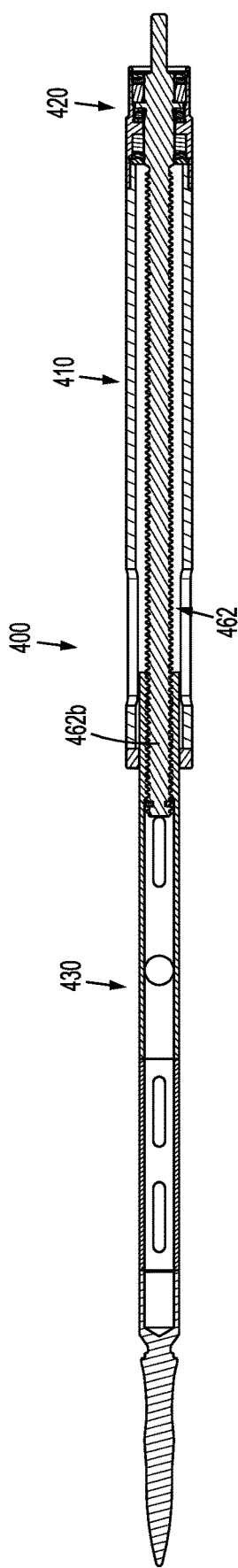
FIG. 37 is a cross-sectional view of the trocar assembly shown in FIG. 33, with the trocar mechanism in an advanced position.
Figure 38:
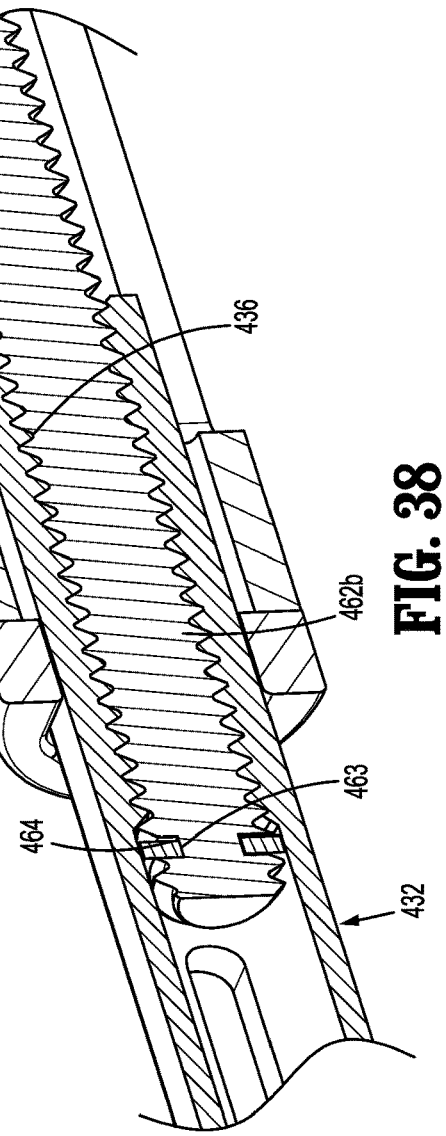
FIG. 38 is a cross-sectional perspective side view of a distal end of a housing assembly of the trocar assembly shown in FIG. 33.
Figure 41:
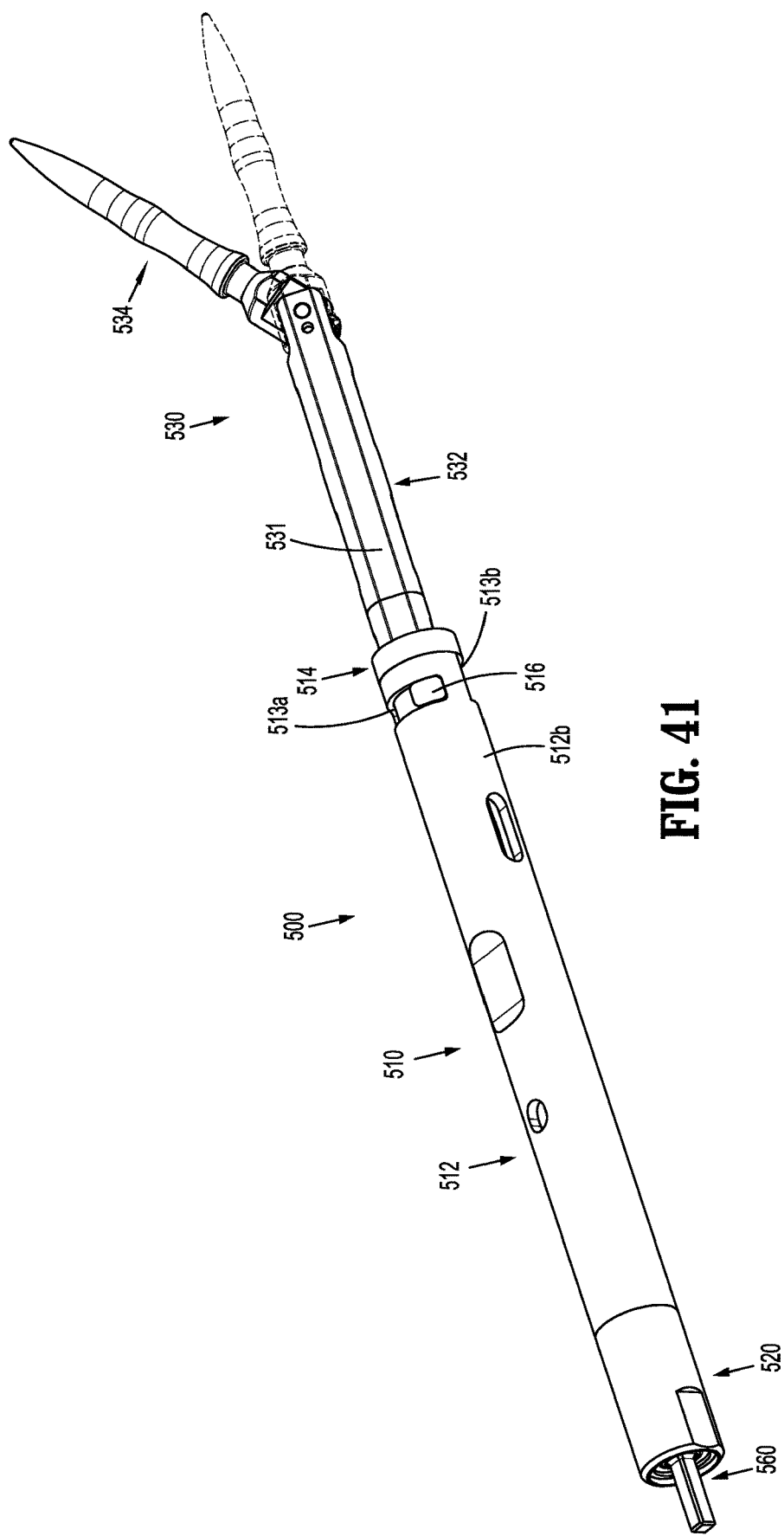
FIG. 41 is a perspective side view of a trocar assembly according to still yet another embodiment of the present disclosure.
Figure 42:
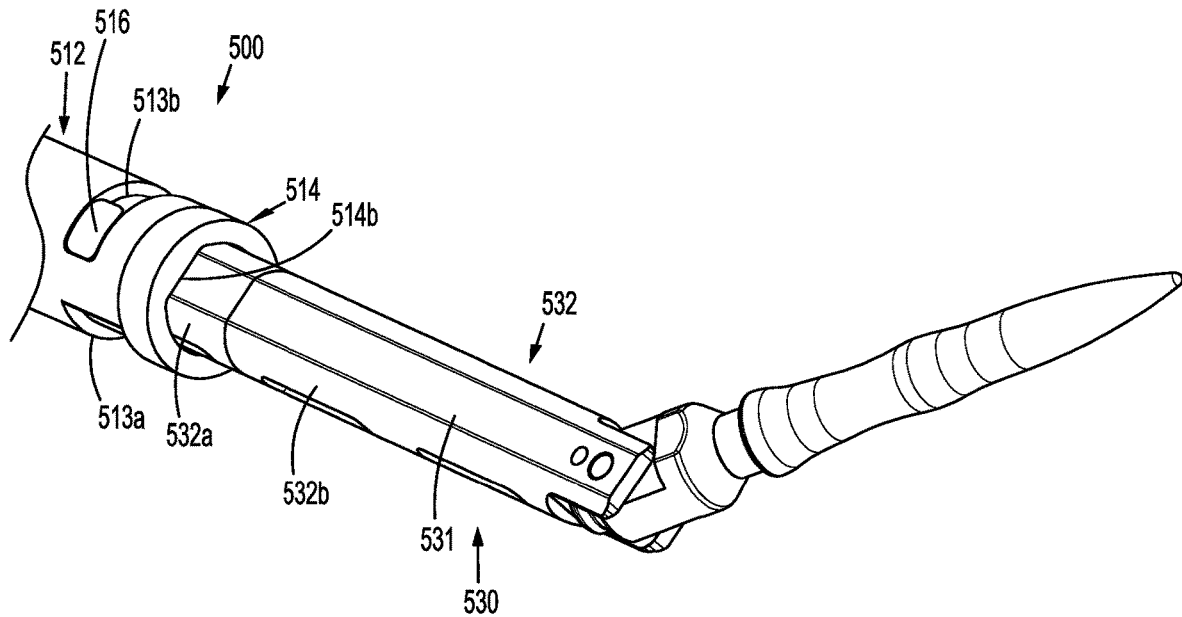
FIG. 42 is a perspective side view of a distal end of the trocar assembly shown in FIG. 41, including a housing assembly and a trocar mechanism extending from the housing assembly.
Figure 43:
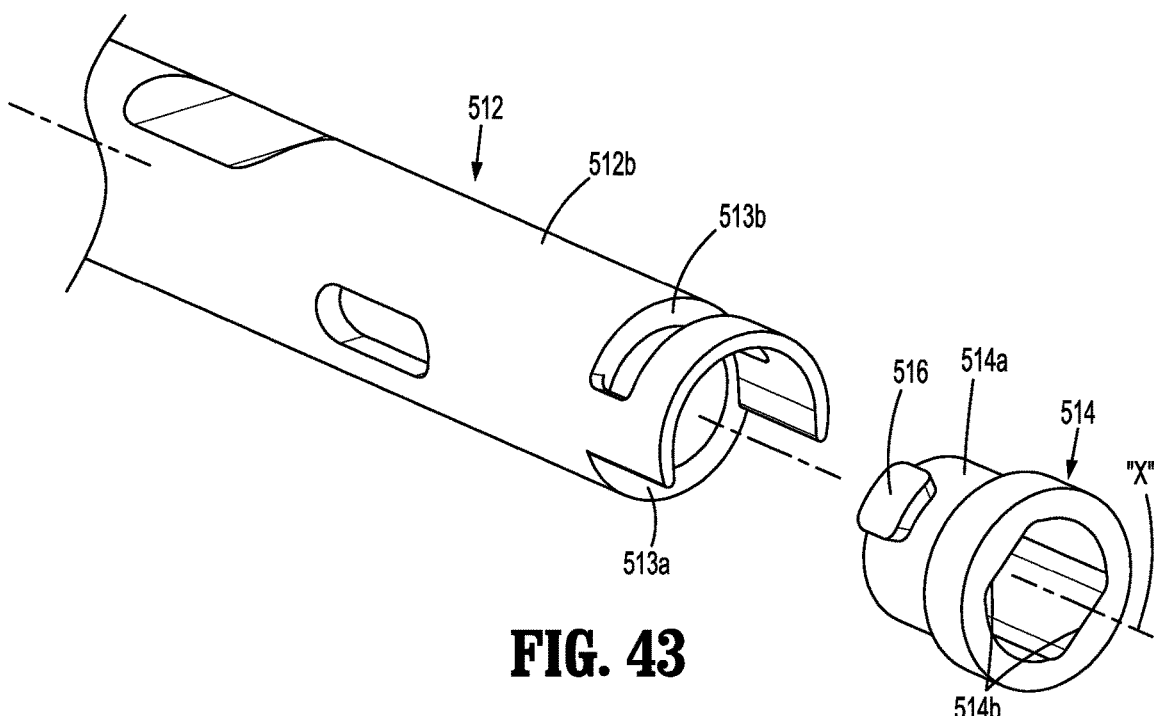
FIG. 43 is a perspective side view of a distal end of the housing assembly shown in FIG. 42, with parts separated.
Figure 44:
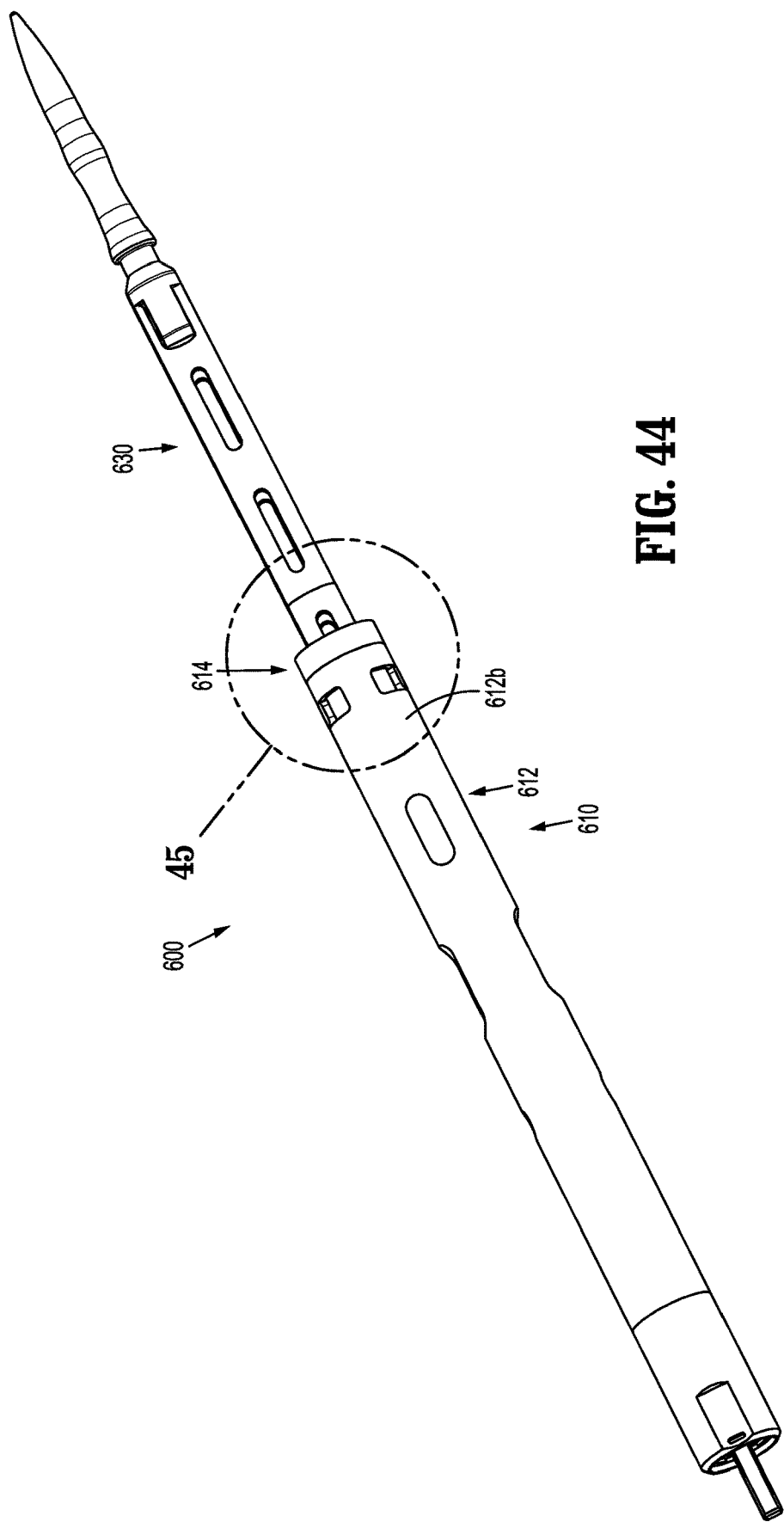
FIG. 44 is a perspective side view of a trocar assembly according to another embodiment of the present disclosure.
Figure 45:
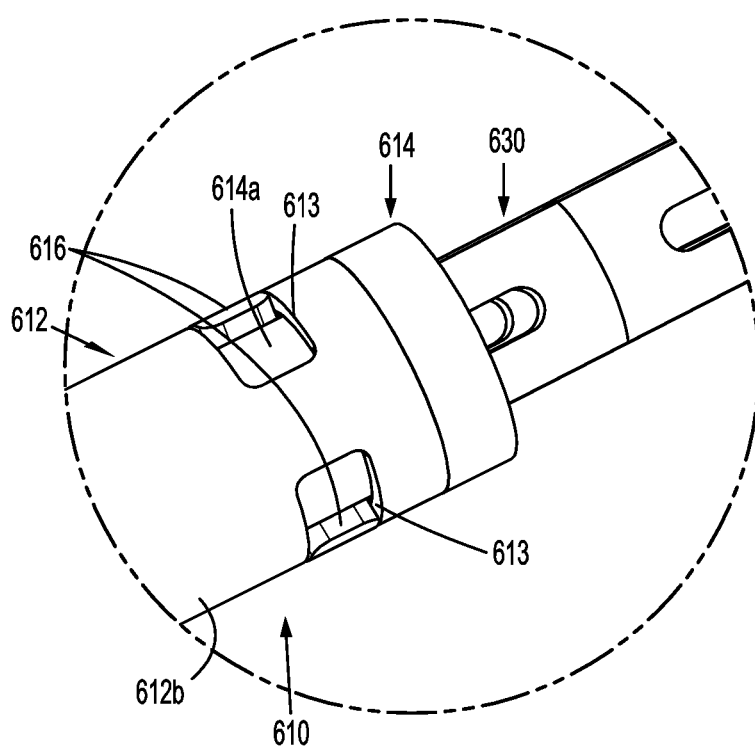
FIG. 45 is an enlarged view of the indicated area of detail shown in FIG. 44.

With reference to FIGS. 37 and 38, during advancement of the trocar mechanism 430, the snap ring 464 engages the threaded inner surface 436 of the tubular member 432 of the trocar mechanism 430 to prevent continued advancement of the trocar mechanism 430. This configuration contains axial loads within the trocar mechanism 430 and the drive member 460. In this manner, the housing assembly 410 of the trocar assembly 400 does not experience an axial load, and therefore does not need to be designed stronger.

When the snap ring 464 engages the threaded inner surface 436 of the tubular member 432, a torque spike in motors of the handle assembly 30 (FIG. 1) will indicate to the handle assembly 30 a distal home position for the trocar mechanism 430. This configuration allows a clinician to calibrate the handle assembly 30 without having to completely retract a previously extended trocar mechanism 430.

With reference to FIGS. 39 and 40, a proximal facing surface 433 of the tubular member 432 of the trocar assembly 400 is configured to engage a stop member 422 disposed between the tubular body 412 of the housing assembly 410 and the bearing assembly 420 of the housing assembly 410. In embodiments, the stop member 422 includes a snap ring. The stop member 422 limits the proximal movement of the trocar mechanism 430 to prevent over-retraction of the trocar mechanism 230 within the housing assembly 410.

Embodiments of trocar assemblies having a trocar mechanism that includes a trocar member configured for articulation and rotation of a trocar member will be described with reference to FIGS. 42-61. Referring initially to FIGS. 41-44, an embodiment of a trocar assembly according to an embodiment of the present disclosure is shown generally as trocar assembly 500. The trocar assembly 500 is substantially similar to the trocar assembly 100 described hereinabove, and will only be described in detail as it relates to the differences therebetween.

The trocar assembly 500 includes a housing assembly 510, a bearing assembly 520 supported on a proximal end of the housing assembly 510, a trocar mechanism 530 slidably disposed within the housing assembly 510, and a drive member 560 rotatably supported within the housing assembly 510 by the bearing assembly 520 for longitudinally moving the trocar mechanism 530 relative to the housing assembly 510.

The housing assembly 510 includes a tubular body 512, and an end cap 514 operably supported on a distal portion 512b of the tubular body 512. More particularly, the distal portion 512a of the tubular body 512 defines a cutout 513a and an arcuate slot 513b. The cutout 513a facilitates connection of the end cap 514 to the tubular body 512 and the arcuate slot 513b receives a post 516 of the end cap 514. The end cap 514 includes a substantially annular body 514a including opposed flattened inner surfaces 514b configured to rotationally fix the trocar mechanism 530 relative to the end cap 514. As will be described in further detail below, the end cap 514 is configured to receive the trocar mechanism 530 therethrough and permit rotation of the trocar mechanism 530 relative to the tubular body 512.

The trocar mechanism 530 of the trocar assembly 500 is configured for longitudinal and rotational movement and articulation relative to the housing assembly 510 of the trocar assembly 500. The trocar mechanism 530 is prevented from overextending from the tubular body 512 of housing assembly 510 by the end cap 514. The trocar mechanism 530 includes a tubular member 532 slidably disposed within the housing assembly 510, and a trocar member 534 pivotally secured to and extending distally from the tubular member 532.

As shown, the tubular member 532 of the trocar mechanism 530 includes proximal and distal sections 532a, 532b. It is envisioned that the tubular member 532 may be monolithic. The tubular member 532 includes elongate flattened surfaces 531a extending along opposed lengths of the tubular member 532. The elongate flattened surfaces 531a of the tubular member 532 of the trocar mechanism 530 align with flattened surfaces 514b of the end cap 514 of a housing assembly 510. The elongate flattened surfaces 531a of the tubular member 532 and the flattened surfaces 514a of the end cap 514 operate together to maintain the trocar member 532 in a fixed rotational orientation relative to the end cap 514.

As noted above, the end cap 514 includes the post 516 received within the arcuate slot 513b in the distal portion 512b of the tubular body 512 of the housing assembly 510. The end cap 514 is configured to rotate about a longitudinal axis "x" of the trocar assembly 500. The rotation of the end cap 514, and therefore rotation of the trocar mechanism 530 received through the end cap 514, is limited by a length of the arcuate slot 513b. The greater the length of the arcuate slot 513b, the greater the degree of rotation of the end cap 514 and the trocar mechanism 530 received through the end cap 514.

Turning to FIGS. 44-48, another embodiment of a trocar assembly is shown generally as trocar assembly 600. The trocar assembly 600 is substantially similar to the trocar assembly 500 described above, and will only be described in detail as it relates to the differences therebetween.

A housing assembly 610 of the trocar assembly 600 includes a tubular body 612, and an end cap 614 operably supported on a distal portion 612b of the tubular body 612. More particularly, the distal portion 612b of the tubular body 612 defines a pair of arcuate slots 613. The arcuate slots 613 receive posts 616 of the end cap 614. The end cap 614 includes a substantially annular body 614a including opposed flattened inner surfaces 614b.

Figure 46:
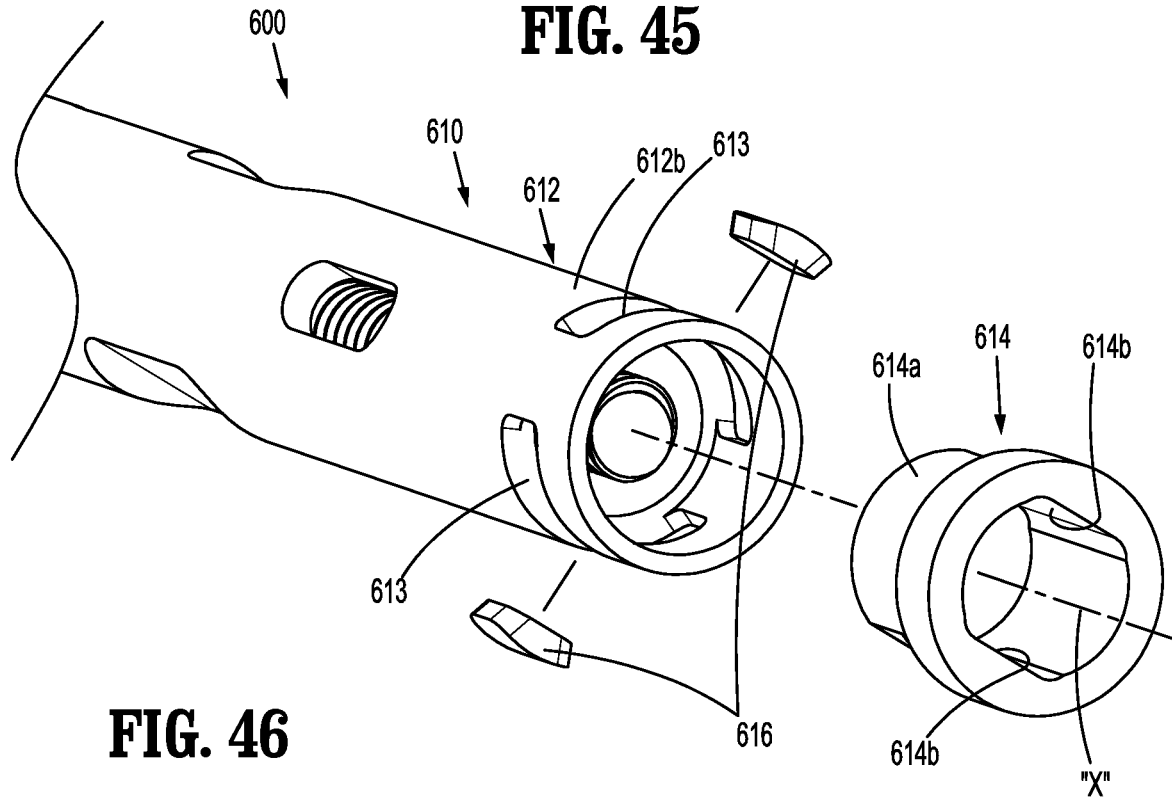
FIG. 46 is a perspective end view of a distal end of a housing assembly of the trocar assembly shown in FIG. 44.
Figure 47:
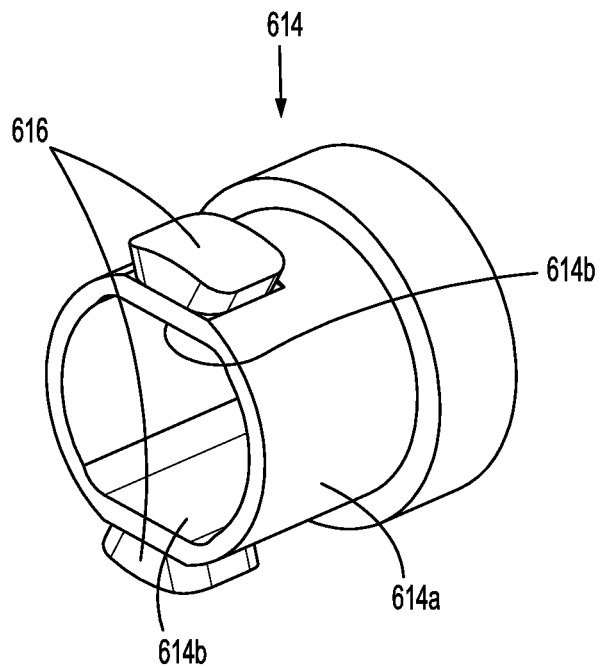
FIG. 47 is a perspective end view of an end cap of the housing assembly shown in FIG. 44.
Figure 48:
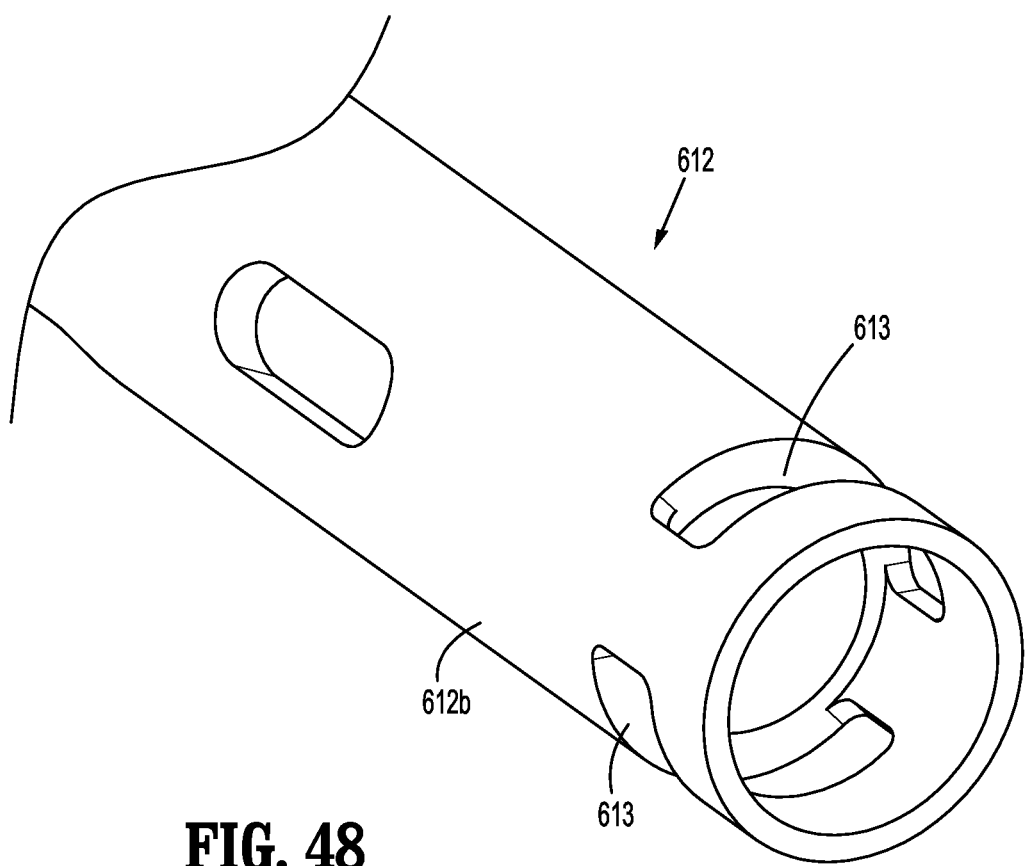
FIG. 48 is a perspective end view of a tubular body of the housing assembly shown in FIG. 46.
Figure 49:
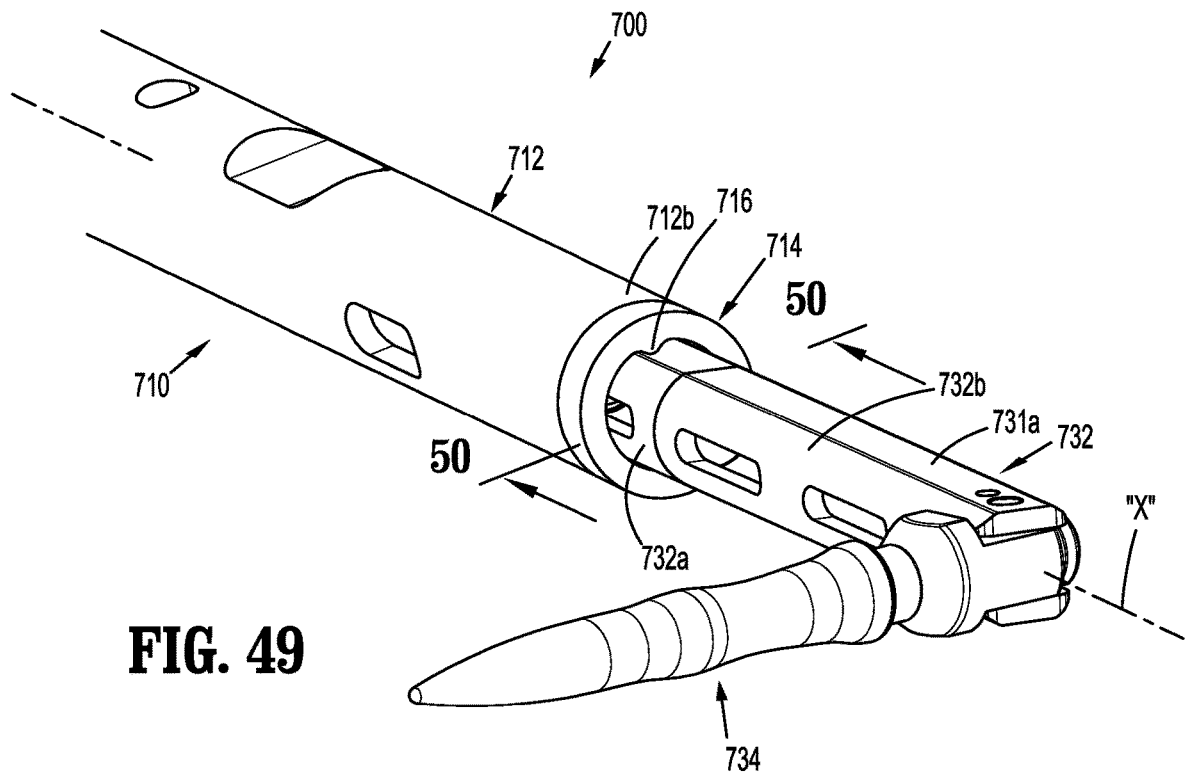
FIG. 49 is a perspective end view of a distal end of a trocar assembly according to still another embodiment of the present disclosure.
Figure 50:
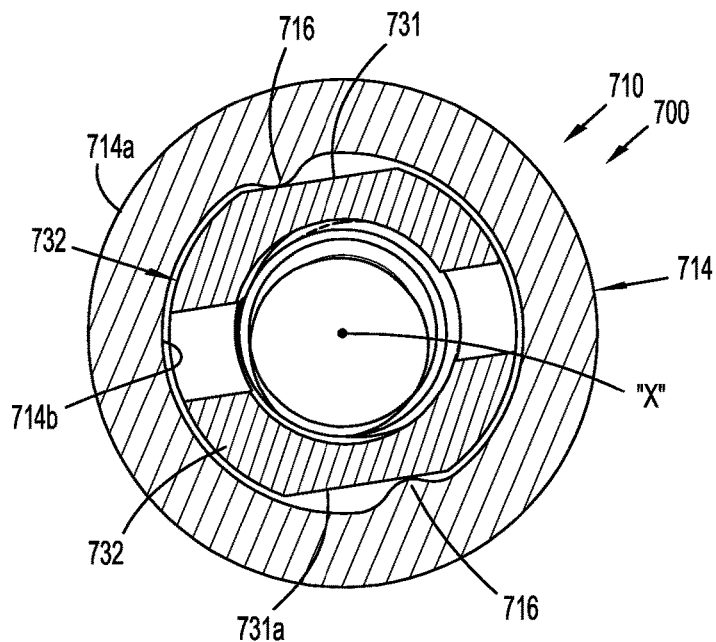
FIG. 50 is a cross-sectional end view taken along line 50-50 shown in FIG. 49.
Figure 51:
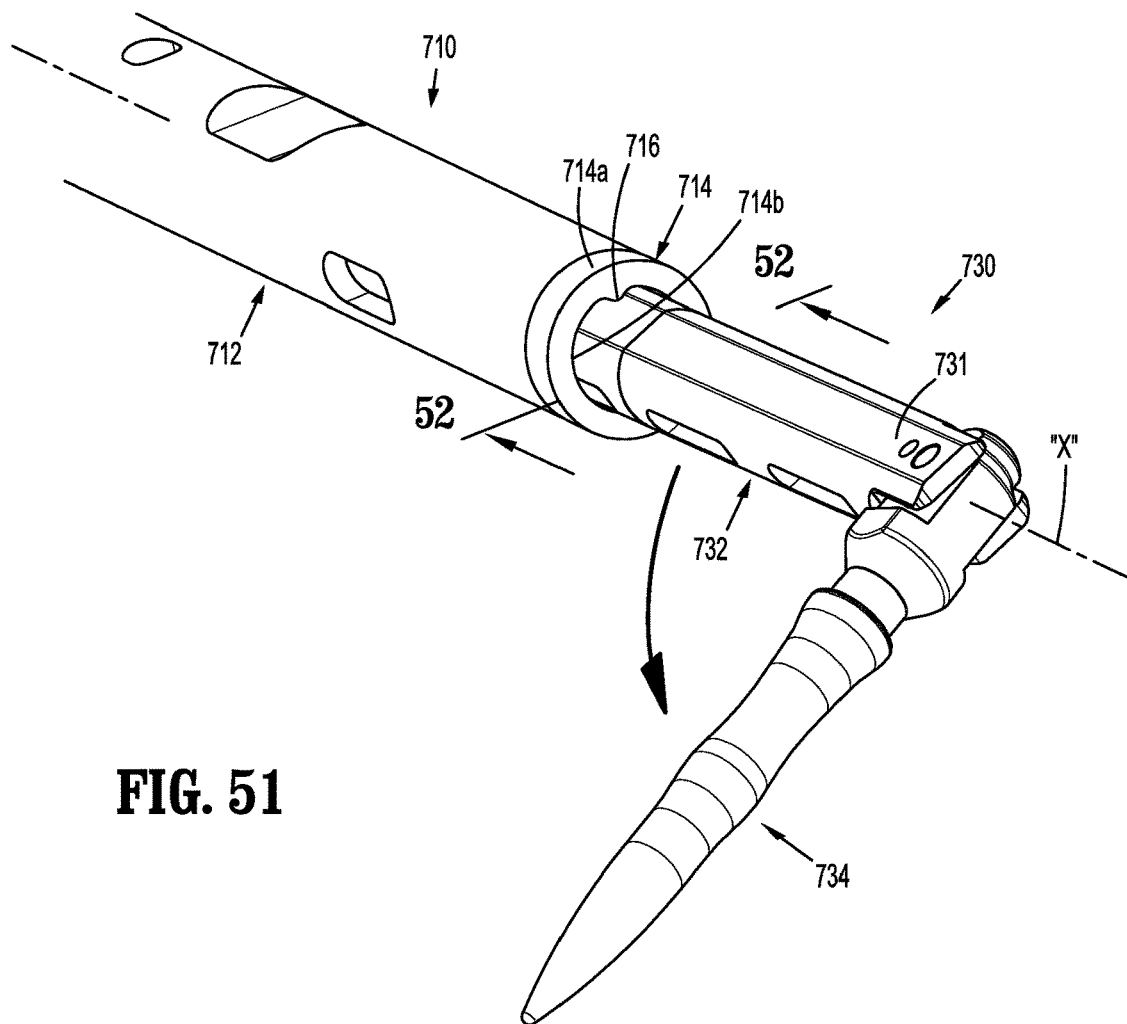
FIG. 51 is a perspective end view of the distal end of the trocar assembly as shown in FIG. 49, with a trocar mechanism is rotated position.

With particular reference to FIG. 46, the posts 616 are secured to the end cap 614 subsequent to the end cap 614 being received within the distal portion 612b of the tubular body 612 of the housing assembly 610. More particularly, the posts 616 are welded, glued, mechanically fastened, or otherwise secured to the annular body 614a of the end cap 614 after the annular body 614a of the end cap 614 is received with the distal portion 612b of the tubular body 612. In this manner, the posts 616 operate to retain the end cap 614 within the tubular body 612 and to permit rotation of the end cap 614 about a longitudinal axis "x" of the trocar assembly 630.

Referring now to FIGS. 49-52, an embodiment of a trocar assembly according to still another embodiment of the present disclosure is shown generally as trocar assembly 700. The trocar assembly 700 is substantially similar to the trocar assemblies 500, 600 described hereinabove, and will only be described in detail as it relates to the differences therebetween.

The trocar assembly 700 includes a housing assembly 710, and a trocar mechanism 730 slidably disposed within the housing assembly 710.

The housing assembly 710 includes a tubular body 712, and an end cap 714 supported on a distal portion 712b of the tubular body 712. The end cap 714 includes a substantially annular body 714a including a pair of nubs 716 extending from an inner surface 714b of the annular body 714a. As will be described in further detail below, the nubs 716 of the end cap 714 correspond with elongated flattened surfaces 731 of the tubular member 732 of the trocar mechanism 730 to permit and limit rotation of the trocar mechanism 730 about a longitudinal axis "x" of the trocar assembly 700 relative to the tubular body 712 of the housing assembly 710.

The trocar mechanism 730 of the trocar assembly 700 is configured for longitudinal and rotational movement and articulation relative to the housing assembly 710 of the trocar assembly 700. The trocar mechanism 730 includes the tubular member 732 slidably disposed within the housing assembly 710 and a trocar member 734 pivotally secured to and extending distally from the tubular member 732.

Figure 52:
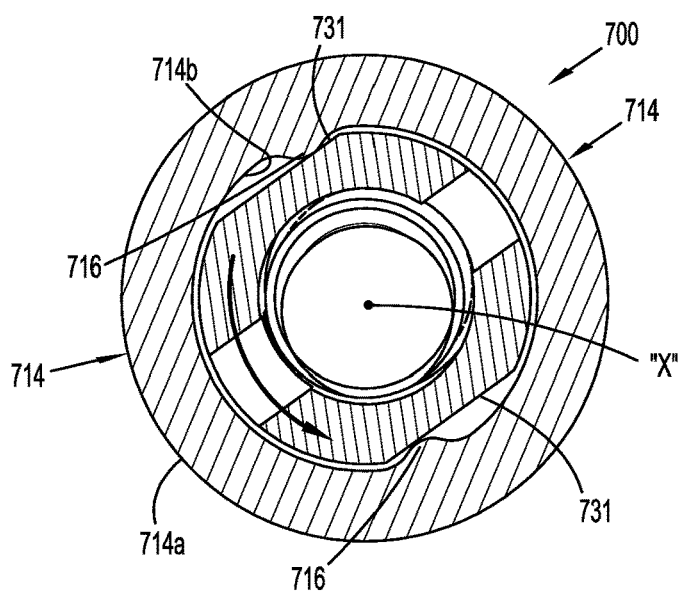
FIG. 52 is a cross-sectional end view taken along line 52-52 shown in FIG. 51.
Figure 53:
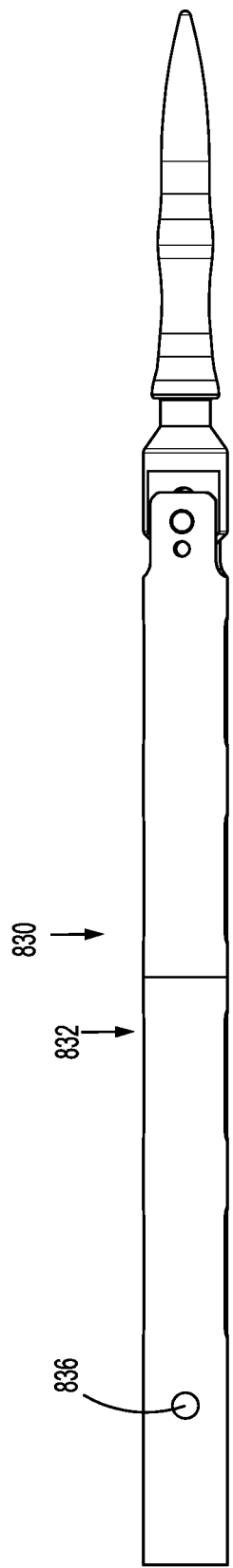
FIG. 53 is a side view of a trocar mechanism of a trocar assembly according to an embodiment of the present disclosure.

The tubular member 732 of the trocar mechanism 730 includes the elongate flattened surfaces 731a extending along opposed lengths of the tubular member 732. The elongate flattened surfaces 731 of the tubular member 732 align with and correspond to the nubs 716 of the end cap 714 of a housing assembly 710. The elongate flattened surfaces 731 of the tubular member 732 provide a clearance that permits reception of the tubular member 732 through the end cap 714. The tubular member 732 is movable from a first rotational orientation relative to the end cap 714 (FIG. 50) to a second rotational orientation relative to the end cap 714 (FIG. 52). Engagement of the nubs 716 of the end cap 714 with the tubular member 732 of the trocar mechanism 730 limits the rotation of the tubular member 732 about the longitudinal axis "x" of the trocar assembly 700.

With reference now to FIGS. 53-56, in another embodiment of the present disclosure, a trocar mechanism 830 includes a tubular member 832 that is slidably receivable with a tubular body 812 of a housing assembly 810. The trocar mechanism 830 includes a pin or post 836 extending outwardly from the tubular member 832. The pin 836 is configured to be received within a longitudinal slot 813 formed in the tubular body 812 of the housing assembly 810.

Figure 54:
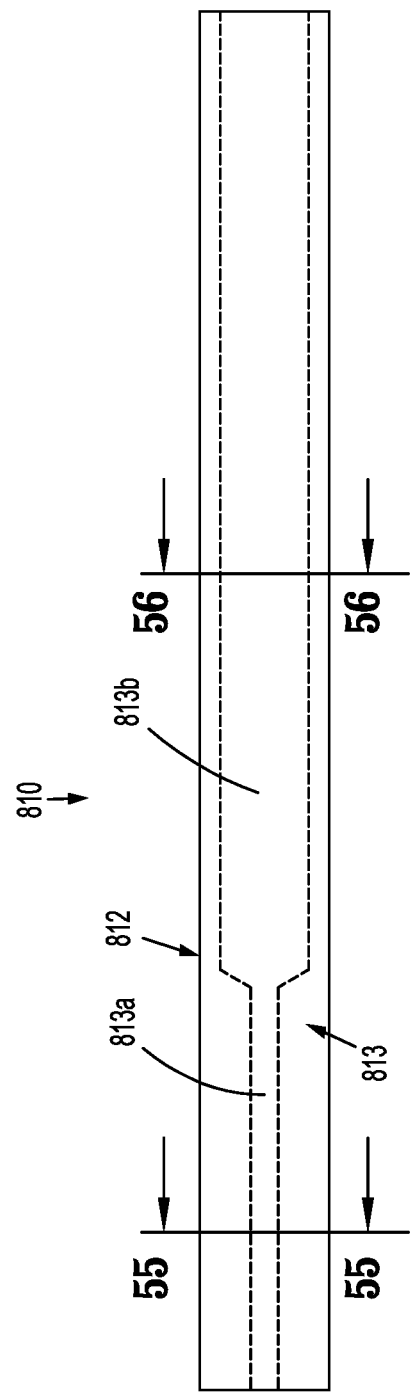
FIG. 54 is a side view of a housing assembly configured for use with the trocar mechanism shown in FIG. 53.

With particular reference to FIG. 54, the longitudinal slot 813 in the tubular body 812 of the housing assembly 810 includes a narrow proximal portion 813a and a wide distal portion 813b. The longitudinal slot 813 is configured to receive the pin 836 of the trocar mechanism 830 when the trocar mechanism 830 is received within the tubular body 812.

Figure 55:
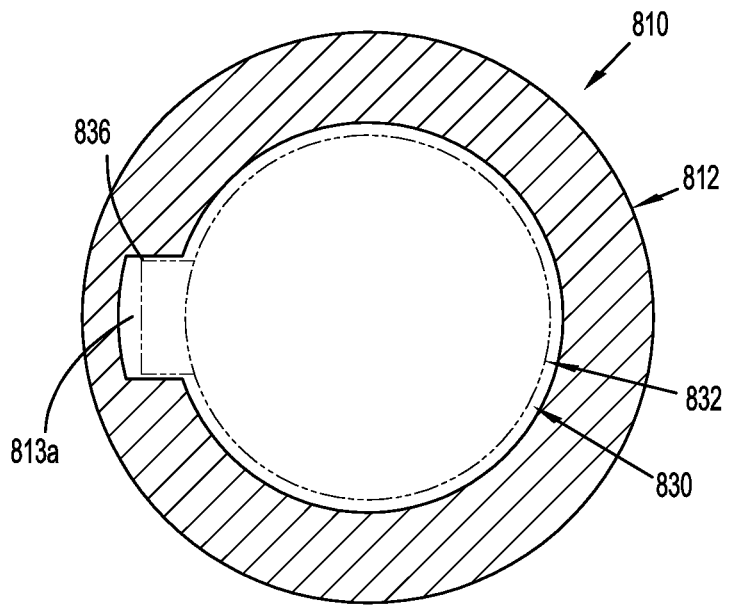
FIG. 55 is a cross-sectional end view taken along line 55-55 shown in FIG. 54.
Figure 56:
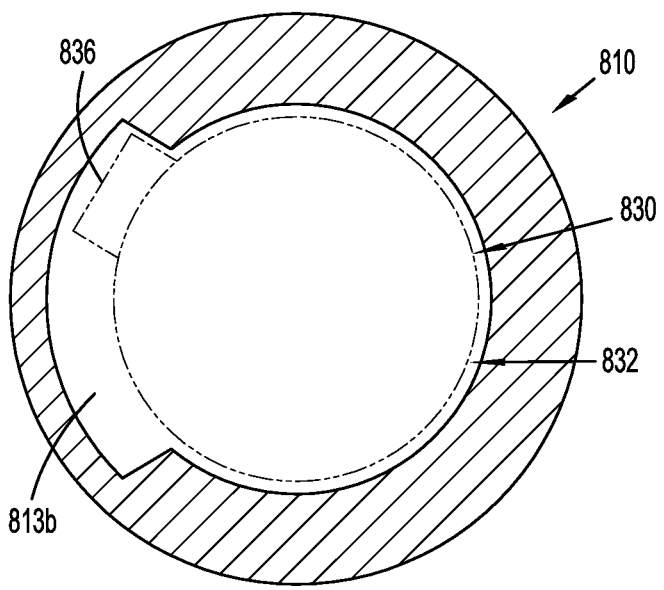
FIG. 56 is a cross-sectional end view taken along line 56-56 shown in FIG. 54.

Turning to FIG. 55, when the pin 836 of the tubular member 832 of the trocar mechanism 830 is received within the tubular body 812 of the housing assembly 810, the trocar mechanism 830 is prevented from rotating through engagement of the pin 836 with the walls of the tubular body 812 defining the narrow proximal portion 813a of the longitudinal slot 813. Conversely, the trocar mechanism 830 is permitted to rotate because of the spacing between the walls of the tubular body 812 defining the wide distal portion 813b of the longitudinal slot 813. In this manner, when the trocar mechanism 830 is in a retracted position within the tubular body 812 of the housing assembly 810, e.g., when the pin 836 is disposed within the narrow proximal portions 813a of the longitudinal slot 813 (FIG. 55), the trocar mechanism 830 is fixed from rotational movement, and when the trocar mechanism is in an advanced position within the tubular body 812, e.g., when the pin 836 is disposed within the wide proximal portion 813b of the longitudinal slot 813 (FIG. 56), the trocar mechanism 830 is free to rotate relative to the tubular body 812.

With reference to FIGS. 57-62, a trocar assembly according to still yet another embodiment of the present disclosure is shown generally as trocar assembly 900. The trocar assembly 900 is similar to the trocar assemblies described hereinabove, and will only be described in detail as it relates to the differences therebetween.

The trocar assembly 900 includes a housing assembly 910, a trocar mechanism 930 slidably disposed within the housing assembly 910, and a drive member 960 rotatably supported within the housing assembly 910 by the bearing assembly 920 for longitudinally moving the trocar mechanism 930 relative to the housing assembly 910.

With particular reference to FIG. 58, the housing assembly 910 of the trocar assembly 900 includes a tubular body 912. The tubular body 912 includes a longitudinal cutout 913 having a narrow proximal portion 913a, a tapered intermediate portion 913b, and a wide distal portion 913c. As will be described in further detail below, the longitudinal cutout 913 permits rotation of the trocar mechanism 930 along a longitudinal axis "x" of the trocar assembly 900. A distal portion 912b of the tubular body 912 defines a notch 915 to facilitate loading of the trocar mechanism 930 within the tubular body 912 of the housing assembly 910.

The trocar mechanism 930 of the trocar assembly 900 is configured for longitudinal and rotational movement relative to the housing assembly 910 of the trocar assembly 900. The trocar mechanism 930 includes a tubular member 932 slidably disposed within the housing assembly 910 and a trocar member 934 secured to and extending distally from the tubular member 932. The trocar mechanism 930 is secured within a tubular body 912 of housing assembly 910 by pin or post 936 extending outwardly from the tubular body 912. The pin 936 is configured to be received within the longitudinal slot 913 of the tubular body 912.

The drive member 960 of the trocar assembly 900 includes an elongate body 962 having a threaded or distal portion 962b. The threaded portion 962b threadingly engages the tubular member 932 of the trocar mechanism 930. Engagement of the tubular member 932 of the trocar mechanism 930 by the elongate body 962 of the drive member 960 secures the trocar mechanism 930 within the tubular body 912 of the housing assembly 910.

As shown in FIGS. 59 and 60, when the trocar mechanism 930 is in an extended or advanced position, the pin 936 extending from the tubular member 932 of the trocar mechanism 930 is disposed within the wide distal portion 913c of the longitudinal slot 913 in the tubular body 912 of the housing assembly 910. When the pin 936 is disposed within the wide distal portion 913c of the longitudinal slot 913, the trocar mechanism 930 is permitted to rotate about a longitudinal axis "x" of the trocar assembly 900 from a first position (FIG. 59) to a second position (FIG. 60).

As the trocar mechanism 930 is retracted within tubular body 912 of the housing assembly 910, e.g., as the drive member 960 rotates in a first direction, the pin 936 of the trocar mechanism 930 passes the tapered intermediate portion 913b of the longitudinal slot 913 and is directed into the narrow proximal portion 913a of the longitudinal slot 913. When the pin 936 is disposed within the tapered intermediate portion 913b of the longitudinal slot 913, the degree of rotation of the trocar mechanism 930 is limited by the walls of the tubular body 912 defining the longitudinal slot 913. When the pin 936 of the trocar mechanism 930 is received within the narrow proximal portion 913a of the longitudinal slot 913, the trocar mechanism 930 is prevented from rotating about the longitudinal axis "x".

Referring now to FIG. 62, the tubular body 912 of the housing assembly 910 is shown as the tubular member 932 of the trocar mechanism 930 is received through the notch 915 (FIG. 58) in the distal portion 912b of the tubular body 912. After receiving the tubular member 932 of the trocar mechanism 930 through the notch 915, the tubular member 932 is aligned with and engaged to the drive member 960 and is threadingly engaged by the drive member 960 to retain the trocar mechanism 930 within the tubular body 912 of the housing assembly 910. The trocar assembly 900 then operates in a traditional manner.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A trocar assembly for releasable engagement with an adapter assembly of a surgical stapling instrument, the trocar assembly comprising:

a housing including a tubular body and defining a longitudinal axis;

an externally threaded member rotatably associated with the housing;

an end cap disposed on a distal end of the tubular body, the end cap including opposed flattened inner first and second surfaces; and a trocar member supported within the housing and received through the end cap, the trocar member including an internal threaded portion and further including opposed flattened outer first and second surfaces corresponding to the opposed flattened inner first and second surfaces of the end cap and distal facing stop surfaces disposed adjacent a proximal end of the opposed flattened outer first and second surfaces, wherein the trocar member is movable between advanced and retracted positions and is rotationally fixed relative to the end cap through engagement of the opposed flattened outer first and second surfaces of the trocar member and the opposed flattened inner first and second surfaces of the end cap, wherein the distal facing stop surfaces of the trocar member engage the end cap to prevent overextension of the trocar member from the housing.

2. The trocar assembly of claim 1, further including a bearing assembly for rotatably supporting the externally threaded member.

3. The trocar assembly of claim 1, further including a stop member for preventing overretraction of the trocar member relative to the housing.

4. The trocar assembly of claim 3, wherein the trocar member includes a proximal facing stop surface for engaging the stop member.

5. The trocar assembly of claim 4, wherein the stop member includes a clip.

6. The trocar assembly of claim 1, wherein the trocar member includes a tip portion and a tubular portion.

7. The trocar assembly of claim 6, wherein the tip portion is configured for releasable engagement with an anvil assembly.

8. The trocar assembly of claim 1, wherein the housing is configured for releasable engagement with a handle assembly.

9. The trocar assembly of claim 6, wherein the opposed flattened outer first and second surfaces of the trocar member extend along a majority of the tubular portion of the trocar member.

10. The trocar assembly of claim 9, wherein the opposed flattened outer first and second surfaces of the trocar member are spaced from the tip portion of the trocar member.

11. A trocar assembly for releasable engagement with an adapter assembly of a surgical stapling instrument, the trocar assembly comprising:
 a housing including a tubular body and a stop member and defining a longitudinal axis;
 an externally threaded member rotatably associated with the housing;
 an end cap disposed on a distal end of the tubular body, the end cap including flattened inner surfaces; and
 a trocar member supported within the housing and received through the end cap, the trocar member including a tubular portion and a tip portion extending from the tubular portion, the tubular portion including an internal threaded portion, flattened outer surfaces corresponding to the flattened inner surfaces of the end cap, distal facing stop surfaces disposed adjacent proximal ends of the flattened outer surfaces, and a proximal facing stop surface, wherein the trocar member is movable between advanced and retracted positions and is rotationally fixed relative to the end cap through engagement of the flattened outer surfaces of the trocar member and the flattened inner surfaces of the end cap, wherein the distal facing stop surfaces of the trocar member engage the end cap to prevent overextension of the trocar member from the housing and the proximal facing stop surface engages the stop member to prevent overretraction of the trocar member into the housing.

12. The trocar assembly of claim 11, further including a bearing assembly for rotatably supporting the externally threaded member.

13. The trocar assembly of claim 11, wherein the stop member includes a clip.

14. The trocar assembly of claim 11, wherein the tip portion is configured for releasable engagement with an anvil assembly.

15. The trocar assembly of claim 11, wherein the housing is configured for releasable engagement with a handle assembly.

16. The trocar assembly of claim 11, wherein the flattened outer surfaces of the trocar member extend along a majority of the tubular portion of the trocar member.

17. The trocar assembly of claim 16, wherein the flattened outer surfaces of the trocar member are spaced from the tip portion of the trocar member.

18. A surgical stapling instrument comprising:
 an adapter assembly; and
 a trocar assembly for releasable engagement with the adapter assembly, the trocar assembly including:
  a housing including a tubular body and defining a longitudinal axis;
  an externally threaded member rotatably associated with the housing;
  an end cap disposed on a distal end of the tubular body, the end cap including opposed flattened inner first and second surfaces; and
  a trocar member supported within the housing and received through the end cap, the trocar member including an internal threaded portion and further including opposed flattened outer first and second surfaces corresponding to the opposed flattened inner first and second surfaces of the end cap and distal facing stop surfaces disposed adjacent a proximal end of the opposed flattened outer first and second surfaces, wherein the trocar member is movable between advanced and retracted positions and is rotationally fixed relative to the end cap through engagement of the opposed flattened outer first and second surfaces of the trocar member and the opposed flattened inner first and second surfaces of the end cap, wherein the distal facing stop surfaces of the trocar member engage the end cap to prevent overextension of the trocar member from the housing.

19. The surgical stapling instrument of claim 18, further including a stop member for preventing overretraction of the trocar member relative to the housing.

20. The surgical stapling instrument of claim 19, wherein the trocar member includes a proximal facing stop surface for engaging the stop member.

* * * * *